United States Patent [19]
Hanauske-Abel et al.

[11] Patent Number: 5,789,426
[45] Date of Patent: Aug. 4, 1998

[54] METHOD FOR THE TREATMENT OF FIBROPROLIFERATIVE DISORDERS BY APPLICATION OF INHIBITORS OF PROTEIN HYDROXYLATION

[75] Inventors: Hartmut M. Hanauske-Abel, Edgewater, N.J.; Timothy A. McCaffrey, New York, N.Y.; Robert Walter Grady, Kinnelon, N.J.

[73] Assignee: Cornell Research Foundation, Inc., Ithaca, N.Y.

[21] Appl. No.: 377,137

[22] Filed: Jan. 20, 1995

[51] Int. Cl.$^6$ .................................. A01N 43/40
[52] U.S. Cl. ............................ 514/348; 546/296
[58] Field of Search ........................ 514/330, 348; 546/296

[56] References Cited

U.S. PATENT DOCUMENTS

| | | |
|---|---|---|
| 4,248,892 | 2/1981 | Kanamara et al. |
| 4,260,599 | 4/1981 | Okazaki . |
| 4,514,420 | 4/1985 | Imada et al. |
| 4,569,943 | 2/1986 | Okazaki et al. |
| 4,604,407 | 8/1986 | Haslanger et al. |
| 4,797,471 | 1/1989 | Teetz et al. |
| 4,897,391 | 1/1990 | Friary . |
| 4,904,675 | 2/1990 | Winter-Mihaly . |
| 4,908,371 | 3/1990 | Moerker et al. ............ 514/318 |
| 4,912,111 | 3/1990 | Sank . |
| 4,937,266 | 6/1990 | Tomikawa et al. |
| 4,997,854 | 3/1991 | Kagan et al. |
| 5,037,839 | 8/1991 | Bickel et al. |
| 5,132,119 | 7/1992 | Lee . |
| 5,158,979 | 10/1992 | Clarkson, Jr. et al. ........ 514/575 |
| 5,182,297 | 1/1993 | Palfreyman . |
| 5,204,338 | 4/1993 | Baader et al. |
| 5,252,608 | 10/1993 | Palfreyman . |
| 5,252,735 | 10/1993 | Morris . |
| 5,260,323 | 11/1993 | Baader et al. |
| 5,518,729 | 5/1996 | Margolin .................... 424/423 |
| 5,620,995 | 4/1997 | Weidmann et al. .......... 514/350 |

FOREIGN PATENT DOCUMENTS

| | | |
|---|---|---|
| 2118176 | 3/1983 | United Kingdom . |
| 92/05190 | 4/1992 | WIPO . |
| WO93/10459 | 5/1993 | WIPO . |

OTHER PUBLICATIONS

Tang et al. "The Inhibitory Effect of Mimosine on Collagen Synthesis", *Toxicon*, 13, pp.339–342 (1975).

N.T. Librojo, et al., "Metabolism of Mimosine and Other Compounds from *Leucaena Leucocephala* by the Chicken," *Nutrition Reports International*, 9(3):217–222 (1974).

H.M. Hanauske–Abel, et al., "Inhibition of the G1–S Transition of the Cell Cycle by Inhibitors of Deoxyhypusine Hydroxylation," *Biochimica et Biophysica Acta*, pp. 1–12, (Jan. 1994).

H.M. Hanauske–Abel, et al., "The Deoxyhypusyl Hydroxylase Inhibitor Mimosine Induces Monocytic Differentiation of HL–60 Cells," Presentation to the Congress of the International Society for Analytical Cytology (Mar. 21–26, 1993).

*Primary Examiner*—Jeffrey Mullis
*Attorney, Agent, or Firm*—Nixon, Hargrave, Devans & Doyle

[57] ABSTRACT

The present invention relates to a method of treating a patient with a fibrotic or fibroproliferative disorder and a method of suppressing formation of collagen and collagen-like substances or biosynthesis of procollagen in living systems by administering to a patient or living system, respectively, an effective amount of a compound of Formulae (I) or (II) and derivatives thereof:

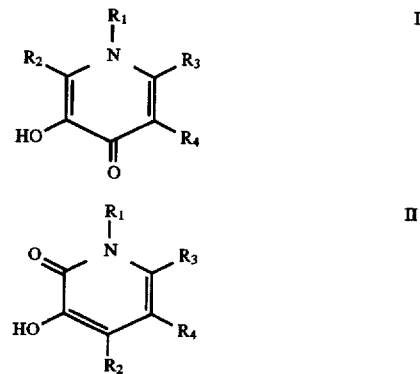

$R_1$, $R_2$, $R_3$, and $R_4$ each individually represent a hydrogen, an alkyl, alkenyl, or alkoxy group containing 1 to about 8 carbon atoms, an aryl, aralkyl, or cycloalkyl group containing about 5 to 12 carbon atoms, or a carboalkoxy or carbamyl group containing up to 8 carbon atoms, or a peptide or peptidomimetic moiety containing 10 to about 30 carbon atoms.

24 Claims, 11 Drawing Sheets

MOLECULAR MIMIKRY OF SUBSTRATE MOTIF BY MIMETIC A

β-TURN OF SUBSTRATE MOTIF

METHOD FOR THE TREATMENT OF FIBROPROLIFERATIVE DISORDERS BY APPLICATION OF INHIBITORS OF PROTEIN HYDROXYLATION

FIELD OF THE INVENTION

This invention relates to the treatment of diseases characterized by the excessive formation of scar tissue and, in particular, to a method for the treating such fibroproliferative disorders by using an effective dose of hydroxypyridone compounds applied topically or systemically.

BACKGROUND OF THE INVENTION

The local formation of a new connective tissue matrix by resident and immigrant cells which on site may also multiply to varying degrees, is part of the physiological, beneficial healing response of all human tissues. In many common, clinically diverse diseases, this fibroproliferative response becomes itself detrimental, however, and produces an abnormal accumulation of fibrocellular scar tissue that further compromises the normal function of the affected tissue and in time, becomes the main cause for morbidity and mortality in these conditions. Examples include, but are not limited to:

All forms of liver fibrosis and cirrhosis, which over the past decades consistently ranks among the ten most common causes of death in the United States. Among the causes that can lead to this condition are: acute and chronic infections, particularly with viruses causing hepatitis; ingestion of toxins, such as alcohol; and autoimmune and genetic abnormalities.

All forms of lung fibrosis, from coal miners' Black Lung Disease to the treatment-induced varieties occurring in cancer patients and premature babies. The fibrocellular scar tissue severely compromises the biophysical parameters of pulmonary function, typically reducing diffusion capacity, vital capacity, and compliance, and progresses relentlessly to respiratory failure and death.

All forms of vascular fibrosis, the process underlying atherosclerosis and diabetic complications. While vascular fibrosis exhibits many varied forms and consequences, typical consequences include angina pectoris, myocardial infarction, stroke, and kidney failure.

All forms of detrimental scarring triggered by interventional therapies, from restenosis of blood vessels and hollow organs to complications after eye surgery. Restenosis of the coronaries, for instance, occurs in about 40% of all balloon angioplasties and atherectomies performed in the United States each year to treat coronary atherosclerosis, leading directly to morbidity and mortality in some 200,000 patients annually.

In the formation and maintenance of this fibrocellular scar tissue, one of the pivotal biochemical events centers on the hydroxylation of the following proteins by specialized intracellular enzymes. These are:

The hydroxylation of the collagens by the enzyme prolyl 4-hydroxylase, forming trans 4-hydroxyproline ("Hyp") residues. The proteins of the collagen family are uniquely distinct from other proteins as only they contain Hyp residues. The collagens constitute the major extracellular building blocks of the fibrocellular scar tissue, and cannot be deposited if Hyp-deficient.

The hydroxylation of the ribosomal protein eIF-5A by the enzyme deoxyhypusine hydroxylase, forming hypusine ("Hps") residues. eIF-5A is required for the biosynthesis of proteins that control cell multiplication, which cannot occur if cells are Hps-deficient.

The hydroxylation of the chaperone LTBP by the enzyme aspartyl/asparaginyl hydroxylase, forming hydroxyaspartate ("Has") and hydroxyasparagine ("Han") residues. LTBP mediates the correct folding of bioactive transforming growth factor β ("TGF-β"), the key hormone controlling formation of fibrocellular scar tissue. Has/Han-deficient LTBP presumably fails in this chaperone function, resulting in the formation of misfolded, biologically inactive TGF-β.

Inhibitors of these protein hydroxylases block the biochemical events that are required for the formation of excessive fibrocellular scar tissue, and therefore have antifibroproliferative properties of clinical importance.

A number of pharmaceutical compounds have been developed to treat various forms of fibrosis or fibroproliferative conditions.

U.S. Pat. No. 4,248,892 to Kanamara, et al. relates to a method for treating fibrosis by administering to a mammal 3,4-dihydroxybenzoic acid and 3,4-dihydroxyphenylacetic acid and their physiologically acceptable salts.

U.S. Pat. No. 4,260,599 to Okazaki discloses the antifibrotic substance P1894B, having specified physical and chemical properties, which is produced by culturing a microorganism belonging to the genus Streptomyces and capable of producing P1894B in culture.

U.S. Pat. No. 4,912,111 to Sank discloses a method for accelerating healing of wounds by oral or topical administration of minoxidil.

U.S. Pat. No. 4,904,675 to Winter-Mihaly discloses pyridine-3-carboxylic acids and esters containing a substituted or unsubstituted 5-tetrazolyl group in the 6-position of the pyridine ring, or tautomers or salts thereof; these compounds are useful as antifibrotic agents as a result of their inhibition of collagen proline hydroxylase.

U.S. Pat. No. 4,937,266 to Tomikawa et al., discloses a method of inhibiting hepatic fibrosis by administering pantethine. It is noted that such administration inhibited an increased prolyl hydroxylase activity in the liver with hepatic fibrosis.

U.S. Pat. No. 4,997,854 to Kagan et al., discloses a method for inhibiting enzymatic activity of lysyl oxidase in situ using 1,2-diamine compounds; these compounds can also be used as anti-fibrotic agents.

U.S. Pat. Nos. 5,182,297 and 5,252,608 to Palfreyman disclose a method of treating fibrotic conditions with 3,3-dihalo-2-propenylamine compounds and their salts, which are inhibitors of lysyl oxidase.

U.S. Pat. No. 5,260,323 to Baader et al., discloses 2,4- or 2,5-disubstituted pyridine N-oxide compounds; these compounds inhibit proline hydroxylase and lysine hydroxylase. Also disclosed is a method of treating a subject in need of a fibrosuppressive or immunosuppressive effect.

U.S. Pat. No. 4,514,420 to Imada et al., discloses a method for treating a mammal suffering from fibrosis with an effective amount of a 2,3-dialkyl-5,6-dimethoxy-p-benzoquinone compound.

U.S. Pat. No. 4,569,943 to Okazaki et al., discloses particular 5-hydroxy-1,4-naphthoquinone compounds and antifibrotic preparations containing them.

U.S. Pat. No. 5,204,338 to Baader et al., discloses a pharmaceutical composition comprising particular oxalylamino acid compounds and their physiologically active salts. These compounds are said to inhibit prolyl hydroxylase and lysine hydroxylase. Also disclosed are methods for influencing metabolism of collagen with effective amounts of these compounds.

U.S. Pat. No. 5,252,735 to Morris discloses particular 2-amino-6-phenyl-4H-pyran-4-one compounds, which are useful as antiatherosclerotic agents and inhibitors of cell proliferation and/or platelet aggregation; preferred compounds contain an N-morpholino substituent in the 2-position of the pyranone ring.

U.S. Pat. No. 5,132,119 to Lee discloses methods of reducing scar tissue and fibromatosis by administering a calcium channel blocker into a wound. The calcium channel blocker is chosen from nifedipine, hydropyridine, verapamil, cobalt chloride, and biologically acceptable cobalt salts.

U.S. Pat. No. 4,797,471 to Teetz et al. discloses use of peptide derivatives as fibrosuppressive agents.

U.S. Pat. No. 5,037,839 to Bickel et al. discusses the use of pyridine-2,4- and -2,5-dicarboxylic acid amides to influence metabolism of collagen.

Despite the existence of all of these substances for treating various forms of fibrosis, the need continues for development of other more effective materials.

SUMMARY OF THE INVENTION

The present invention relates to a method of treating a patient with a fibrotic or fibroproliferative disorder and a method of suppressing formation of collagen and collagen-like substances or biosynthesis of procollagen in living systems by administering to a patient or living system, respectively, an effective amount of a compound of Formulae (I) or (II) and derivatives thereof:

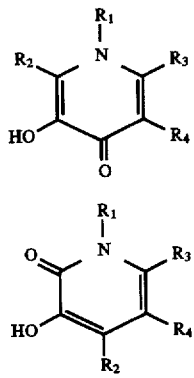

$R_1$, $R_2$, $R_3$, and $R_4$ each individually represent a hydrogen, an alkyl, alkenyl, or alkoxy group containing 1 to about 8 carbon atoms, an aryl, aralkyl, or cycloalkyl group containing about 5 to 12 carbon atoms, or a carboalkoxy or carbamyl group containing up to 8 carbon atoms, or a peptide or peptidomimetic moiety containing 10 to about 30 carbon atoms.

While not wishing to be bound by theory, since the compounds of the Formulae (I) and (II), according to this invention, inhibit the enzymatically catalyzed hydroxylations of proteins, they are apt to prevent the maturation of such proteins which do not become biologically functional until in their hydroxylated forms. These hydroxylation-dependent proteins are, for instance, the collagens, the ribosomal initiation factor eIF-5A, and LTBP, the chaperone for synthesis of bioactive TGF-β. If their hydroxylation is suppressed by inhibition of the enzymes which catalyze this reaction, i.e. prolyl 4-hydroxylase, deoxyhypusyl hydroxylase, and aspartyl/asparaginyl hydroxylase, respectively, these proteins are rendered unable to function. As the functions of these hydroxylation-dependent proteins converge in the clinical disease group of fibrotic and fibroproliferative conditions, the protein hydroxylase inhibitors of Formulae (I) and (II) are suitable instruments to control and treat such conditions pharmacologically.

BRIEF DESCRIPTION OF THE DRAWINGS

In FIG. 3a, the effect on the human enzyme was determined by measuring in proliferating cultured B-lymphocytes the covalent incorporation of tritiated spermidine-derived label into cellular protein, after standard hydrolysis, chromatographic separation of amino acids, and expression of the results relative to uninhibited controls. In FIG. 3b, a standard chromatographic elution profile is shown as obtained from cultured human smooth muscle cells ("SMC"), grown out of coronary atherosclerotic lesions and metabolically labeled in the absence and presence of L-mimosine. In its absence, the tritiated spermidine-derived label occurs in a peak corresponding to Hps, whereas in its presence the label is shifted to the unhydroxylated precursor of Hps, i.e., deoxyhypusine.

DETAILED DESCRIPTION OF THE INVENTION

The present invention relates to a method of treating a patient with a fibrotic or fibroproliferative disorder and a method of suppressing formation of collagen and collagen-like substances or biosynthesis of procollagen in living systems by administering to a patient or living system, respectively, an effective amount of a compound of Formulae (I) or (II) and derivatives thereof:

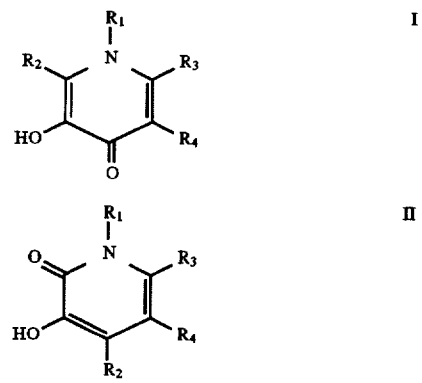

$R_1$, $R_2$, $R_3$, and $R_4$ each individually represent a hydrogen, an alkyl, alkenyl, or alkoxy group containing 1 to about 8 carbon atoms, an aryl, aralkyl, or cycloalkyl group containing about 5 to 12 carbon atoms, or a carboalkoxy or carbamyl group containing up to 8 carbon atoms, or a peptide or peptidomimetic moiety containing 10 to about 30 carbon atoms.

The alkyl, alkenyl, alkoxy, aryl, aralkyl, and cycloalkyl groups represented by $R_1$, $R_2$, $R_3$, and $R_4$ can be substituted or unsubstituted. Examples of unsubstituted alkyl groups are methyl, ethyl, propyl, isopropyl, butyl, sec-butyl, pentyl, hexyl, and the like. Unsubstituted alkenyl groups can be 2-propenyl, 2-butenyl, 3-butenyl, 2-methyl-2-butenyl, and the like. Unsubstituted alkoxy groups can be methoxy, ethoxy, propoxy, isopropoxy, and the like. Unsubstituted aryl groups can be phenyl or naphthyl. Aralkyl groups can be, for example, benzyl and phenylethyl. Cycloalkyl groups can be cyclopentyl, cyclohexyl, 4-methyl cyclohexyl, and the like. For substituted alkyl, alkenyl, alkoxy, aryl, aralkyl, and cycloalkyl groups, substituents can include, for example, halo, alkoxy, amino, hydroxy, carboxy, carboalkoxy, and carbamyl. Aryl and aralkyl groups can, in addition, contain alkyl substituents.

Figure 8:
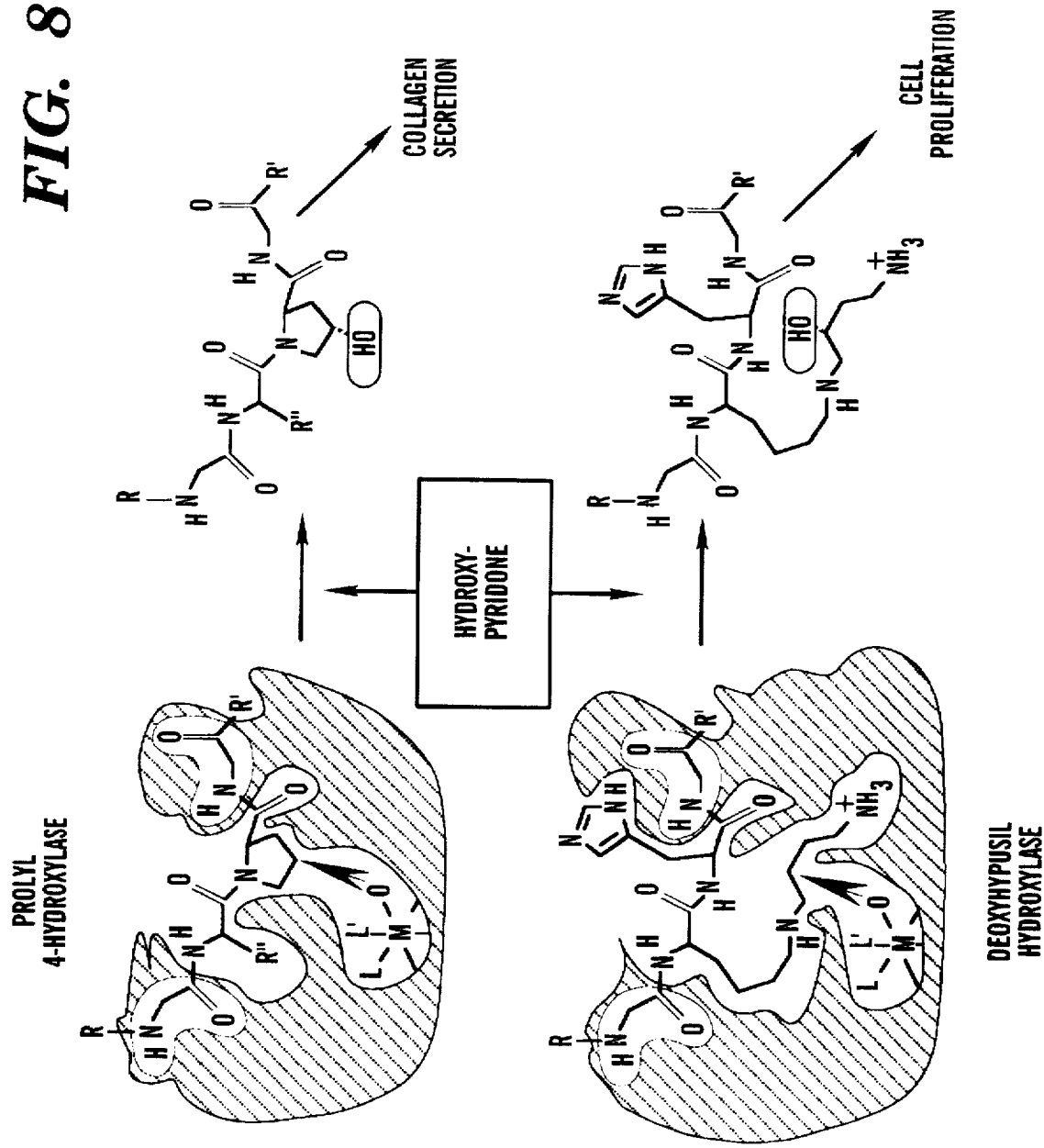
FIG. 8 depicts the anti-fibroproliferative mode of action of compounds of Formulae (I) or (II) mediated by inhibition of protein hydroxylases, as schematically shown here for prolyl 4-hydroxylase and deoxyhypusyl hydroxylase. The diagram emphasizes the similarity in active site organization between these two particular enzymes with regard to i) their respective peptide substrate, which in each case displays a -Gly-x-y-Gly motif (glycine residues highlighted in gray); ii) the orientation of this peptide substrate in relation to the active site metal (M); and iii) the organization of the active site; where the metal is located within a pocket inside of the protein proper, symbolized by the hatched area, and in this manner shielded from the outside and accesible only to inhibitors of a certain geometry. The active site metal (M), is thought to generate and orient a reactive oxygen atom species (O) for stereospecific attack on the prolyl C4 and the deoxyhypusyl C9 atoms, in this way mediating hydroxylation (arrows). It is claimed that compounds of Formulae (I) or (II) are able to block its role in catalysis. Inhibition of prolyl 4-hydroxylase directly suppresses the hydroxyproline-dependent formation and secretion of triple helical collagens, whereas inhibition of deoxyhypusyl hydroxylase compromises cell proliferation.

The post-translational hydroxylations of the hydroxylation-dependent proteins occur within highly specific motifs of their primary structure. For example, these motifs are -G-x-m*-G- for prolyl 4-hydroxylase, -G-m*-x-G- for deoxyhypusyl hydroxylase, and -C-x-m*-x(4)-[F/Y]-x-C-x-C- for aspartyl/asparaginyl hydroxylase, with m* indicating the position of the substrate residue to be modified by hydroxylation, i.e. prolyl, deoxyhypusyl, or aspartyl/asparaginyl, respectively, G being glycine, x indicating the presence of any residue, C being cysteine, F being phenylalanine, and Y being tyrosine. It is generally accepted that all protein hydroxylases, when hydroxylating artificial substrates of the correct motif alone, show low or very low affinity for such substrates. This is attributed to the fact that these short motifs do not present themselves to the enzymes' active site in the conformation known to be optimal for hydroxylation, a conformation easily assumed, however, within the structure of a larger peptide or the native substrate protein. To overcome this lack of affinity, suitable peptide motifs or their corresponding peptidomimetics, termed 'carriers', can be equipped with a reactive moiety, termed 'warhead', that is precisely positioned to interact with the active site metal ion common to all these protein hydroxylases (see FIG. 8). Directed to the enzyme of interest by the appropriate carrier, the warhead interacts with the active site metal, locking the carrier to the enzyme and in this manner, enhances the inhibitory capacity of the carrier which otherwise may be either non- or only weakly inhibitory. This concept is termed "warhead strategy" and is applicable to the rational design of all motif-guided protein hydroxylase inhibitors. As to Formulae (I) and (II), such a warhead strategy is effected where $R_1$, $R_2$, $R_3$, and/or $R_4$ is a peptide or peptidomimetic moiety containing 10 to about 30 carbon atoms. The warhead strategy requires that the warheads, which may themselves be inhibitory for the protein hydroxylases, must fit their respective active sites and must be reasonably stable under biological conditions, e.g., not susceptible to redox cycling. Consequently, warheads can consist of moieties of Formulae (I) or (II), for instance, properly positioned on a suitable carrier for optimal anti-fibroproliferative effect.

Table I contains representative forms of the hydroxypyridone compounds of Formula (I) of the present invention:

TABLE I

| Trivial name | $R_1$ | $R_2$ | $R_3$ | $R_4$ |
|---|---|---|---|---|
| L-mimosine | —CH₂CH(COOH)NH₂ | H | H | H |
| HK1, CP20, L1, DMHP | —CH₃ | —CH₃ | H | H |
| HK2, CP94 | —CH₂CH₃ | —CH₂CH₃ | H | H |
| CP93 | —CH₃ | —CH₂CH₃ | H | H |
| CP96 | —(CH₂)₂OCH₃ | —CH₂CH₃ | H | H |
| HK26, CP21 | —CH₂CH₃ | —CH₃ | H | H |
| HK27, CP22 | —(CH₂)₂CH₃ | —CH₃ | H | H |
| HK16 | —CH₂CH=CH₂ | —CH₃ | H | H |
| CP23 | —CH(CH₃)₂ | —CH₃ | H | H |
| CP40 | —(CH₂)₂OH | —CH₃ | H | H |
| CP41 | —(CH₂)₃OH | —CH₃ | H | H |
| CP42 | —(CH₂)₄OH | —CH₃ | H | H |
| CP43 | —(CH₂)₅OH | —CH₃ | H | H |
| CP44 | —(CH₂)₂NH₂ | —CH₃ | H | H |
| CP51 | —(CH₂)₂OCH₃ | —CH₃ | H | H |
| HK15 | —CH₂OCH₂CH₃ | —CH₃ | H | H |
| CP54 | —CH(CH₃)CH₂OCH₃ | —CH₃ | H | H |
| CP52 | —(CH₂)₃OCH₂CH₃ | —CH₃ | H | H |
| | —CH₃ | H | —CH₃ | H |
| | —CH₃ | H | H | —CH₃ |
| | —CH₂CH(COOC₂H₅)—NH₂ | H | H | H |

Table II contains representative forms of the hydroxypyridone compounds of Formula (II) of the present invention:

TABLE II

| $R_1$ | $R_2$ | $R_3$ | $R_4$ |
|---|---|---|---|
| —CH₃ | —CH₃ | H | H |
| —CH₂CH₃ | —CH₂CH₃ | H | H |
| —CH₃ | —CH₂CH₃ | H | H |
| —(CH₂)₂OCH₃ | —CH₂CH₃ | H | |
| —CH₂CH₃ | —CH₃ | H | H |
| —(CH₂)₂CH₃ | —CH₃ | H | H |
| —CH₃ | H | —CH₃ | H |
| —CH₃ | H | H | —CH₃ |

Compounds of Formula (I)

Compounds of Formula (I) are synthesized by one of several general procedures.

Method A

This method is adapted from Kontoghiorghes and Sheppard (*Inorg. Chim. Acta* 136:L11–L12 (1987)), which is hereby incorporated by reference. In brief, a 3-hydroxy-4-pyrone is refluxed for approximately 6 hours with three equivalents of a primary amine dissolved in an appropriate solvent. The reaction mixture is decolorized with charcoal, filtered, and the filtrate evaporated to give a dark residue. The residue is recrystallized from one to three times from an appropriate solvent to yield a solid product with a narrow melting point and an NMR spectrum consistent with the structure anticipated.

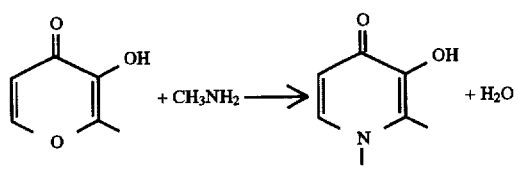

In particular, 3-hydroxy-2-methyl-4-pyrone (10 g) was refluxed for 6.5 hours with three equivalents of aqueous methylamine (40%) in 200 ml of water. The reaction mixture was allowed to cool after which decolorizing charcoal was added to the solution, and the mixture was stirred for 0.5 hours. After filtration, the solvent was evaporated under reduced pressure, and the solid residue recrystallized three times from water to yield 1,2-dimethyl-3-hydroxypyrid-4-one (HK-1, L1, CP20, DMHP) as fine white needles.

In a slight modification of this procedure, N-carboxymethyl-3-hydroxy-2-methylpyrid-4-one is prepared as described by Zhang et al., *Can. J. Chem.* 70:763–770 (1992) which is hereby incorporated by reference. One equivalent of 3-hydroxy-2-methyl-4-pyrone and two equivalents of glycine are dissolved in hot distilled water, the pH is adjusted to approximately 9 with 8N sodium hydroxide, and the reaction mixture is heated under reflux for 20 hours. After cooling and decolorizing with charcoal, approximately half of the solvent is removed under vacuum and 6N hydrochloric acid is added to reduce the pH to approximately 3. A yellow solid precipitates which yields the product as off-white crystals after two recrystallizations from water (mp 258°–260° C.).

Method B

This method is adapted from GB Patent No. 2,118,176A to Hider et al., which is hereby incorporated by reference. In brief, a 3-hydroxy-4-pyrone is converted to the corresponding 3-benzyloxy-4-pyrone via reaction with benzyl chloride. A methanolic solution of the pyrone is added to an aqueous solution of sodium hydroxide after which benzyl chloride is added and the reaction mixture refluxed for approximately 6 hours. The solvent is evaporated under reduced pressure, water is added, and then the product is extracted into an appropriate organic solvent. After washing, the extract is dried over anhydrous magnesium sulfate and the solvent evaporated to yield the crude 3-benzyloxy derivative which is used in the next step without further purification. To a solution of the 3-benzyloxy compound in an appropriate solvent is added a slight excess of primary amine. The reaction mixture is stirred at room temperature for approximately 6 days after which it is acidified to pH 2 with concentrated hydrochloric acid and evaporated to dryness. The residue is washed with water and extracted into an appropriate organic solvent which is then dried over magnesium sulfate and evaporated to dryness. To the residue is added hydrobromic acid. This reaction mixture is heated on a steam bath for 30 minutes and then recrystallized from water to yield the N-substituted 3-hydroxypyrid-4-one. The product melts sharply and has an NMR spectrum consistent with the desired product.

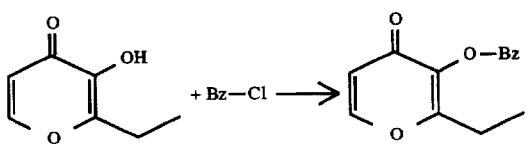

-continued

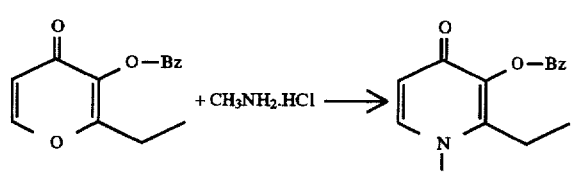

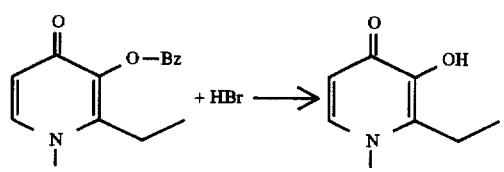

In particular, 2-ethyl-3-hydroxy-4-pyrone (24.7 g) in 225 ml of methanol is added to 25 ml of water containing 7.5 g of sodium hydroxide. To this solution is added benzyl chloride (25.5 g) and the mixture is then refluxed for 6 hours. Upon cooling, the solvent is removed under reduced pressure. The residue is treated with 50 ml of water and then extracted three times with 25-ml aliquots of dichloromethane. The combined extracts are washed twice with 5% (w/v) sodium hydroxide, then twice with 25 ml of water and dried over magnesium sulfate. Evaporation of the solvent yields crude 3-benzyloxy-2-ethyl-4-pyrone. This crude pyrone (24.4 g) and 1.56 g of methylamine hydrochloride are then dissolved in 300 ml of aqueous ethanol (100 ml) containing 2 g of sodium hydroxide. The solution is stirred at room temperature for 6 days, acidified to pH 2 with concentrated hydrochloric acid, and then evaporated to dryness. The residue is washed with water and extracted twice into chloroform (50 ml). The combined extracts are dried over anhydrous magnesium sulfate and evaporated to dryness yielding 3-benzyloxy-2-ethyl-1-methylpyrid-4-one. To 2 g of this pyrid-4-one is added concentrated hydrobromic acid (10 ml). The reaction mixture is heated on a steam bath for 30 minutes and the product recrystallized from water to yield 2-ethyl-3-hydroxy-1-methylpyrid-4-one.

Method C

This method is adapted from that of Bartulin et al., *J. Heterocyclic Chem.* 29:1017–1019 (1992), which is hereby incorporated by reference. A 3-benzyloxy-4-pyrone, prepared as in Method B, is added to an ethanolic solution of aqueous ammonia. The reaction mixture is stirred for approximately 3 days, concentrated under reduced pressure, triturated with acetone, and the solid recrystallized from ethanol to yield the corresponding 3-benzyloxypyrid-4-one. To a solution of this pyrid-4-one in aqueous ethanol containing one equivalent of sodium hydroxide was added an equivalent of n-alkyl bromide. The reaction mixture was heated under reflux for 24 hours after which it was cooled, concentrated under reduced pressure, and extracted with an appropriate solvent. After washing, the organic phase with water, it is dried over magnesium sulfate. The product is obtained upon concentration of the solution under reduced pressure. Crude 1-alkyl-3-benzyloxypyrid-4-one in acetic acid containing 40% hydrobromic acid is then heated on a steam bath for 30 minutes. The 1-alkyl-3-hydroxypyrid-4-one precipitates and is subsequently recrystallized from benzene in good yield with a narrow melting point and appropriate NMR spectrum.

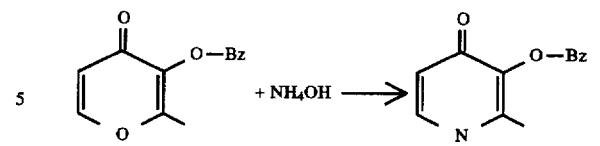

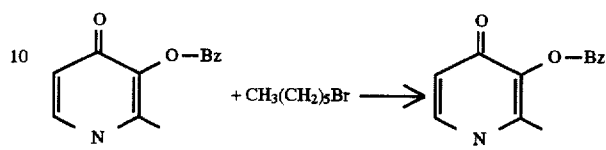

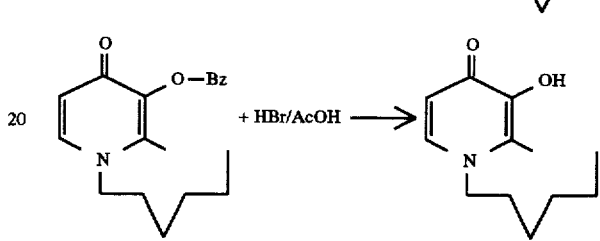

In particular, 3-benzyloxy-2-methyl-4-pyrone was prepared as described in Method B. A solution containing 15.3 g of the pyrone, 160 ml of aqueous ammonia (25%) and 80 ml of ethanol is stirred at room temperature for 3 days. The solvent is removed under reduced pressure and some acetone added. The solid which precipitates is collected by filtration and recrystallized from ethanol to yield (80%) 3-benzyloxy-2-methylpyrid-4-one with a melting point of 162°–163° C. A solution containing 0.125 moles of the pyrid-4-one, 0.125 moles of n-hexyl bromide, 0.125 moles of sodium hydroxide, 25 ml of water, and 200 ml of ethanol is heated under reflux for 24 hours. After removal of the solvent under vacuum, the residue is extracted with ethyl ether. The etherial solution is washed with water yielding a precipitate which is crystallized from benzene after drying to give 3-benzyloxy-1-hexyl-2-methylpyrid-4-one (95%, mp 46° C.). A solution of this compound in 80 ml of acetic acid containing 40% hydrobromic acid is then heated on a steam bath for 30 minutes. The product is filtered off and crystallized from benzene to yield 1-hexyl-3-hydroxy-2-methylpyrid-4-one in 70% yield.

Compounds of Formula (II)

Compounds of Formula (II) are synthesized by the general procedure outlined in GB Patent No. 1,118,176A to Hider et al., which is hereby included by reference. In brief, 2,3-dihydroxypyridine is mixed with an organic halide in a sealed tube and heated at 140° C. for 24 hours. The tube is then cooled in an acetone/dry ice bath and opened. The excess halide is poured off and water is added to the dark residue. Sulfur dioxide gas is bubbled through the mixture until the aqueous phase becomes clear. The pH of the reaction mixture is then adjusted to approximately 6 with sodium carbonate, and the resulting solution is extracted with an appropriate solvent after saturation with ammonium sulfate. The organic extracts are dried over anhydrous sodium sulfate and concentrated under reduced pressure to yield a solid which gives the desired N-substituted 3-hydroxypyrid-2-one after crystallization from petroleum ether.

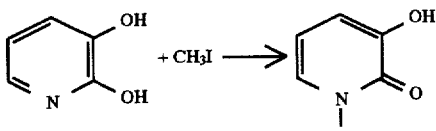

In particular, 5.6 g of 2,3-dihydroxypyridine in 20 ml of methyl iodide are heated in a sealed tube at 140° C. for 24 hours. The tube is cooled in acetone/dry ice, opened and the excess methyl iodide poured off. Distilled water (10 ml) is added and the solution treated with sulfur dioxide until clear. The pH of the reaction mixture is adjusted to 6 with aqueous sodium carbonate (1M) after which the resulting solution is saturated with ammonium sulfate followed by extraction with chloroform until the chloroform layer fails to give a blue color with aqueous ferric chloride. The combined extracts are dried over sodium sulfate after which the solvent is removed under reduced pressure and the residue crystallized from petroleum ether to give 3-hydroxy-1-methylpyrid-2-one.

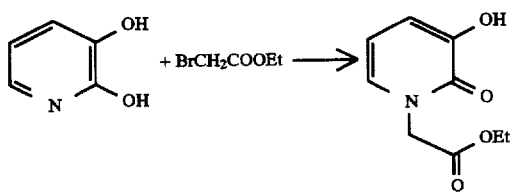

A related compound, 1-ethoxycarbonylmethyl-3-hydroxy-pyrid-2-one, is prepared by heating a mixture of 2,3-dihydroxypyridine (5 g) and 20 ml of ethylbromoacetate in a sealed tube at 140° C. for 24 hours, as described by GB Patent No. 4,585,780 to Hider et al., which is hereby incorporated by reference. After cooling in solid $CO_2$, the tube is opened, the reaction mixture poured off, and evaporated to dryness under vacuum to yield a yellow solid. Recrystallisation from water yields the product as white crystals (5.4 g), MP 141°–151° C.

By applying the warhead strategy, suitable compounds, e.g. of Formulae (I) or (II), also can be used attached to carriers as defined above, which mimic the substrate motif of the protein hydroxylases. This optimizes the interaction of such compounds with the active site metal ion of these enzymes in order to achieve antifibrotic and antiproliferative effects. Carriers can be the physiological substrate motifs in their peptide form, or peptidomimetic molecules of these motifs that are biologically stable and cell membrane permeable.

Examples are:

1. A peptide carrier of the substrate motif G-x-y-G-type for inhibition of deoxyhypusyl hydroxylase, to be equipped with an appropriate compound of Formulae (I) or (II), such as 1-carboxymethyl-3-hydroxy-2-methylpyrid-4-one or 1-carboxymethyl-3-hydroxypyrid-2-one, respectively. Peptides of the sequence Ac-Dab(A)-H-G-OH, in which A denotes a radical of the Formulae Ia or IIa

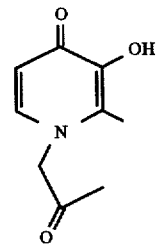

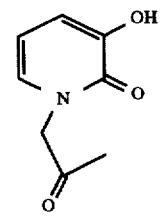

are prepared in analogy to the general procedure for synthesis of catecholpeptides as outlined in U.S. Pat. No. 4,797,471 to Teetz et al. which is hereby incorporated by reference. There, Ac is acetate, Dab is 2,4-diaminobutyric acid, A is a residue constituting a warhead, H is histadine, G is glycine, and OH is hydroxyl. The starting materials are Ac-Dab-H-G-O-Bzl and the 3-benzyloxy derivative of the appropriate hydroxypyridone, all synthesized by conventional methods. The C-terminal substituent '-O-Bzl' is benzyl ester. The peptide and the appropriate 3-benzyloxypyridone derivative are coupled using a carbodiimide protocol, i.e., they are dissolved in dimethylformamide in the presence of 1-hydroxybenzotriazole and N-ethylmorpholine, and allowed to proceed at room temperature for 18 hours after addition of dicyclohexylcarbodiimide, as described by U.S. Pat. No. 4,797,471 to Teetz et al. The solvent is removed by vacuum, the residue immediately dissolved in methanol, and, after addition of Pd/C, hydrogenolytically cleaved. When the cleavage is complete, which is checked by thin layer chromatography, the catalyst is removed by filtration, and the filtrate concentrated in vacuo.

2. A peptidomimetic carrier of the substrate motif G-x-y-G for inhibition of deoxyhypusyl hydroxylase, to be equipped with an appropriate moiety of Formulae (I) or (II), where y indicates the presence of any residue. The β-turn mimetic A

Figure 2B:
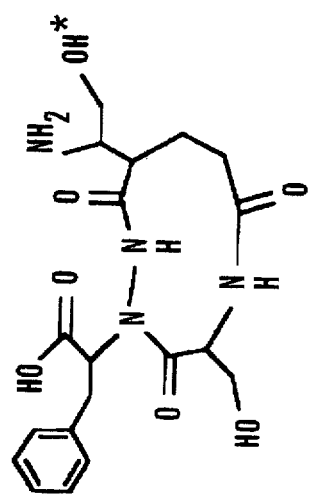
FIG. 2b shows the molecular mimikry of the substrate motif by mimetic A.

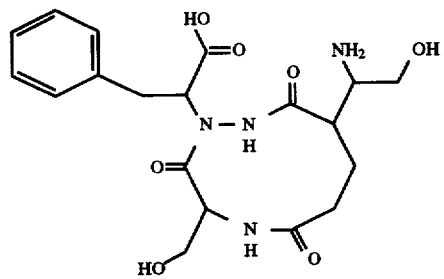

was synthesized according to the method published by Chen et al., Proc. Natl. Acad. Sci. USA 89:5872–5876 (1992), which is hereby incorporated by reference. Briefly, the precursor azetidinone was prepared analogous to Salzmann et al., J. Am. Chem. Soc. 102:6161–63 (1980) and to Williams et al., J. Am. Chem. Soc. 111:1073–83 (1989), which are hereby incorporated by reference. Intermediate reaction steps are: i) mixed anhydride coupling of azetidinone to O-benzyl serine benzyl ester, followed by hydrogenolytic cleavage of the benzyl ester to generate intermediate A; ii) reaction of intermediate A with Z-protected hydrazinophenylalanine, giving intermediate B; iii) using intermediate B, reductive closure, saponification, and hydrogenolytic deprotection of the side chain-protecting groups afforded the product A which was tested to verify its ability to interact as a peptidomimetic with the enzyme (see FIG. 2). For the purposes of using this compound as a carrier, appropriate warheads, e.g. a moiety of Formulae (I) or (II), can be introduced in the course of building up the ring structure A.

The anti-fibroproliferative compounds of the present invention can be used to treat a wide variety of fibrotic disorders. These disorders can be endogenously occurring, e.g. in sclerodermia, caused by genetic abnormalities, e.g. in certain forms of neonatal liver fibrosis, due to environmental agents (infectious/occupational/toxic/traumatic), such as in liver cirrhosis or lung fibrosis or post-burn scaring, or the tissue response to medical interventions, such as restenosis of blood vessels after angioplasty, or lung fibrosis after cancer therapy, or scaring after eye surgery. Other disorders include but are not limited to hepatic fibrosis and cirrhosis, renal fibrosis, myelofibrosis, and keloids. These compounds can be administered orally; parenterally, i.e. by subcutaneous, intravenous, or intramuscular injection; intraperitoneally; or by topical application, such as instillation into the walls of blood vessels or hollow organs, or by application to the mucous membranes of the nose, throat, bronchial tree, or eyes, etc. They may be administered alone or with suitable pharmaceutical carriers, and can be in solid or liquid form such as tablets, capsules, powders, solutions, suspensions, or emulsions. The dosage of the active compound depends on the species of warm-blooded animal, the body weight, age, and mode of administration. Appropriate dosage results in improvement of the clinical disease and, in particular, causes an arrest or a reduction in the mass of the fibrocellular scar tissue or a decrease of the products it secrets, such as the levels of procollagen peptides in serum. The anatomical location of the fibroproliferative scar tissue to be treated is the single most important determinant for the mode of administration and the pharmaceutical preparation of these compounds. Hepatic fibrosis and cirrhosis require an orally active compound rapidly extracted by the liver from the portal blood leaving the gut, which are established pharmacokinetic characteristics of, for instance, a compound like HK1 (CP20, L1, DMHP). Pulmonary fibrosis, on the other hand, is more directly addressed by an intravenously administered agent possibly in combination with inhalation of an aerosolized compound, whereas vascular restenosis or cutaneous scarring can be managed by local application regimen.

The pharmaceutical products of the present invention are prepared by dissolving, mixing, granulating, or tablet-coating processes which are known per se.

For oral administration, the active compounds or their physiologically tolerated derivatives such as salts, esters, or amides, are mixed with the additives customary for this purpose, such as vehicles, stabilizers, or inert diluents, and converted by customary methods into a suitable form for administration, such as tablets, coated tablets, hard or soft gelatin capsules, aqueous, alcoholic, or oily suspensions, or aqueous, alcoholic or oily solutions. Examples of suitable inert vehicles are conventional tablet bases such as lactose, sucrose, or cornstarch in combination with binders like acacia, cornstarch, gelatin, or with disintegrating agents such as cornstarch, potato starch, alginic acid, or with a lubricant like stearic acid or magnesium stearate. Examples of suitable oily vehicles or solvents are vegetable or animal oils, such as sunflower oil or fish-liver oil. Preparations can be effected both as dry and as wet granules.

For parenteral administration (subcutaneous, intravenous, intraarterial, or intramuscular injection), the active compounds or their physiologically tolerated derivatives such as salts, esters, or amides, are converted into a solution, suspension or emulsion, if desired with the substances customary and suitable for this purpose, such as solubilizers or other auxiliaries. Examples are: sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycol or polyethylene glycol, are preferred liquid carriers, particularly for injectable solutions.

For use as aerosols, the active compounds or their physiologically tolerated derivatives such as salts, esters, or amides, may be dissolved or suspended in a physiologically acceptable liquid and packaged in a pressurized aerosol container together with suitable propellants, for example, hydrocarbon propellants like propane, butane, or isobutane with conventional adjuvants. The antifibrotic agents may also be administered from a non-pressurized container such as a nebulizer or atomizer.

For topical administration to external or internal body surfaces, e.g. in the forms of creams, gels, or drops, etc., for treatment of fibroproliferative conditions involving, for instance, the skin or the eye, the active compounds or their physiologically tolerated derivatives such as salts, esters, or amides, are prepared and applied as solutions, suspensions, or emulsions in a physiologically acceptable diluent with or without a pharmaceutical carrier.

EXAMPLES

General Methodology

The inhibitory action of the substances according to the invention, for example on collagen secretion or cell proliferation, can be tested in direct assays of the enzymes mediating the pivotal protein hydroxylations for these biological processes, such as prolyl 4-hydroxylase and deoxyhypusyl hydroxylase. This entails the enzymatic hydroxylation of the appropriate protein precursor, either by the cellular or the purified enzyme, in the presence or absence of compounds of Formulae (I) or (II), with concomitant determination of co-substrate utilization by these enzymes or subsequent isolation of the hydroxylated amino acid and its unhydroxylated precursor. In this manner, the inhibitory potency of any given compound can be measured in the cell-free system, in cell culture, or in tissue, and is expressed as the inhibitory dose that gives a 50% reduction of the enzyme-mediated reaction (ID50). Enzyme is tested in analogy to the method of A. Abbruzzese, H. M. Hanauske-Abel, et al., *Biochem. Biophys. Acta*, 1077, 159–166 (1991) and of K. Majamaa, H. M. Hanauske-Abel, et al., *Eur. J. Biochem.* 138, 239–245 (1984), which are hereby incorporated by reference. Table III lists the ID50 values of some of the compounds according to the invention, using purified human prolyl 4-hydroxylase and cellular human deoxyhypusyl hydroxylase as representative protein hydroxylases.

TABLE III

[Structure: pyridone ring with R1 on N, R2 at position 2, HO at position 3, O at position 4]

| | R1 | R2 | Prolyl 4-hydroxylase ID50 (purified) | Deoxyhypusyl hydroxylase ID50 (cellular) |
|---|---|---|---|---|
| L-Mimosine | $-CH_2CH(NH_2)COOH$ | H | 120 | 65 |
| -ethyl ester | $-CH_2CH(NH_2)COOC_2H_5$ | H | 145 | |
| HK-1 | $-CH_3$ | $-CH_3$ | 133 | 90 |
| HK-2 | $-CH_2CH_3$ | $-CH_2CH_3$ | 145 | 50 |
| HK-15 | $-CH_2OCH_2CH_3$ | $-CH_3$ | 210 | 60 |
| HK-16 | $-CH_2CH=CH_2$ | $-CH_3$ | 150 | 50 |
| HK-26 | $-CH_2CH_3$ | $-CH_3$ | 130 | 58 |
| HK-27 | $-(CH_2)_2CH_3$ | $-CH_3$ | 155 | 50 |

The examples which follow serve to illustrate the present invention without intending to restrict it to them.

Example 1

Inhibition of Purified Human Prolyl 4-Hydroxylase

The inhibiting effect of hydroxypyridones on the collagen-hydroxylating enzyme was studied in a cell-free system.

Methods
Assay of Purified Human Prolyl 4-Hydroxylase

The native $\alpha_2\beta_2$-tetrameric enzyme was purified to homogeneity by poly(L-proline) affinity chromatography and DEAE chromatography from the supernatant of *Spodoptera frugiperda* insect cells cotransfected with recombinant baculovirus transfer vectors for both the human $\alpha$- and $\beta$-subunits. Enzyme activity was determined by trapping of $^{14}CO_2$ released from 2-oxo[1-$^{14}C$]glutarate] according to the procedure of Majamaa, et al., *Eur. J. Biochem.*, 138:239–245 (1984), which is hereby incorporated by reference. Briefly, all incubations were run for 60 minutes at 37° C. in a final volume of 1.0 ml per test sample, containing 0.1 µg enzyme, 0.1 mg heat-denatured (Pro-Pro-Gly)$_{10}$×9 $H_2O$ as hydroxylatable substrate, 0.1 mM 2-oxo[1-$^{14}C$] glutarate] adjusted to 60.000 dpm by mixing with the unlabeled 2-oxoglutarate as cosubstrate, and cofactors (1.6 mM ascorbate, 0.05 mM ferrous sulfate, 0.08 mM dithiothreitol, 2 mg bovine serum albumin, 5 µL catalase). Assays are performed with only one of the active compounds at any given time.

Results

Figure 1:
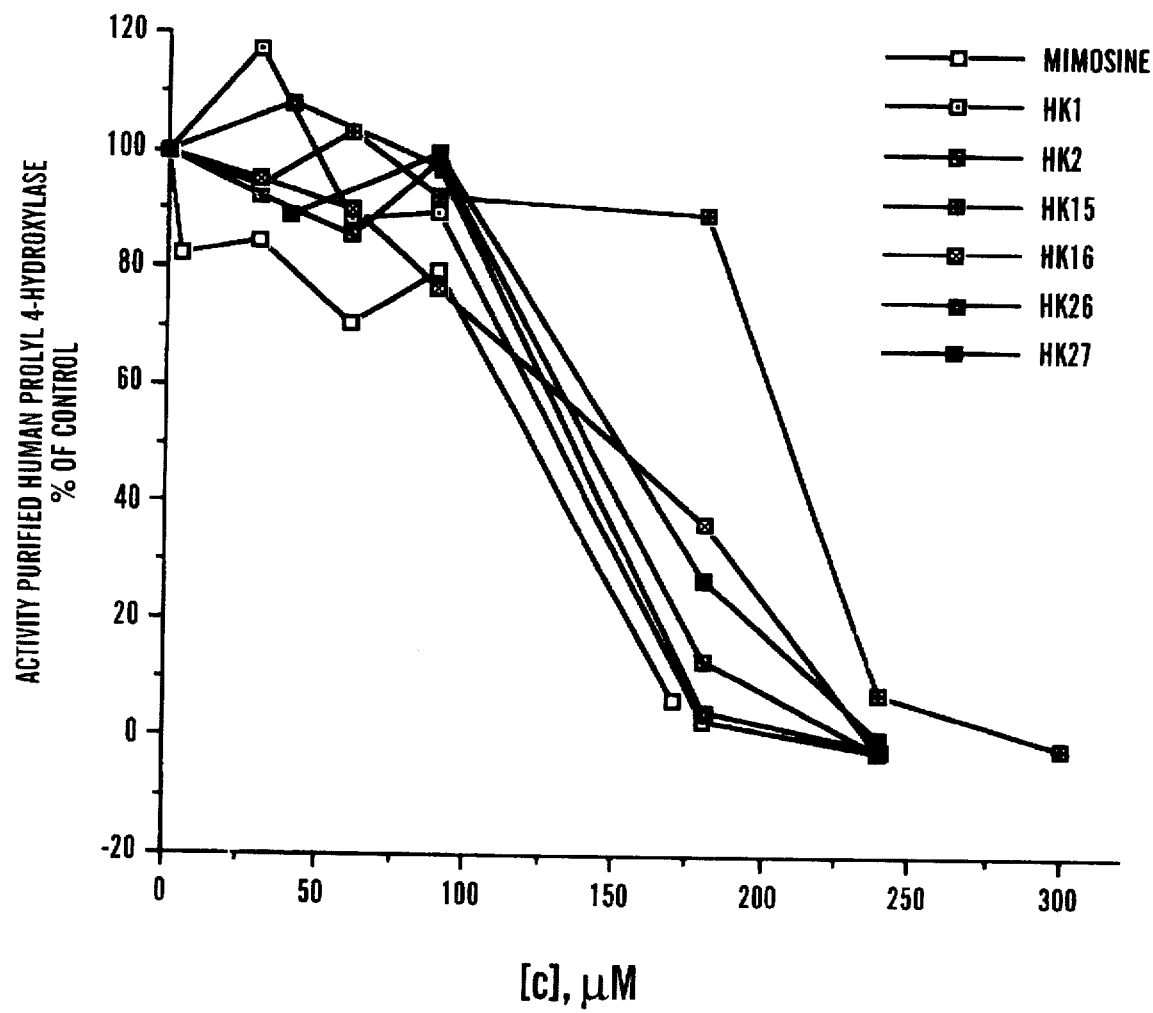
FIG. 1 shows the inhibition of purified human prolyl 4-hydroxylase, relative to uninhibited enzyme activity, by several representative hydroxypyridone compounds. The effect on the enzyme was determined in a cell-free system by measuring the oxidative decarboxylation of its cofactor 2-oxoglutarate via release of radiolabeled carbon dioxide in a standard reaction mixture also containing ascorbate, ferrous sulfate, and unhydroxylated peptide substrate.

All of the seven representative hydroxypyridone compounds were found to be potent prolyl 4-hydroxylase inhibitors (FIG. 1). It is prior established knowledge that suppression of prolyl 4-hydroxylase leads to an inability of collagen proteins to form their biologically active structure, the characteristic 'collagen triple helix', and leads to reduced collagen secretion and/or extracellular collagen fibril formation, i.e., leads to a reduction of the fibrous component within fibroproliferative scar tissue. The actual effect of representative hydroxypyridones on secretion of collagens prominent in the scarring process, collagens type I and III, was subsequently examined in cultured human cells known to be causally involved in fibroproliferative diseases.

Example 2

Inhibition of Purified Rat Deoxyhypusyl Hydroxylase

The inhibiting effect of a model peptidomimetic, suitable to serve as carrier for hydroxypyridone warheads, on the activity of the purified eIF-5A-hydroxylating enzyme was studied in a cell-free system.

Methods
DOHH Assay

Enzyme activity was purified and determined as described by Abbruzzese et al., *J. Biol. Chem.* 261:3085–9 (1986), which is hereby incorporated by reference. Briefly, the enzyme is offered labeled deoxyhypusine-containing eIF-5A precursor. Following standard incubation conditions, the conversion into hypusine residue is measured by chromatographic amino acid separation after protein hydrolysis.

Results

Mimetic A was designed, and then synthesized, to covalently stabilize the optimal - $\beta$ turn conformation known to be characteristic for -G-x-y-G- motifs when occurring within the structure of the native substrate proteins of deoxyhypusyl hydroxylase or the collagen hydroxylases. At the same time, mimetic A lends itself to serve as a carrier for a reactive moiety to be positioned at the hydroxylation site for interaction with the active site metal ion. In the case of mimetic A, this reactive moiety can be attached at the site indicated by the asterisk in FIG. 2b.

Figure 2A:
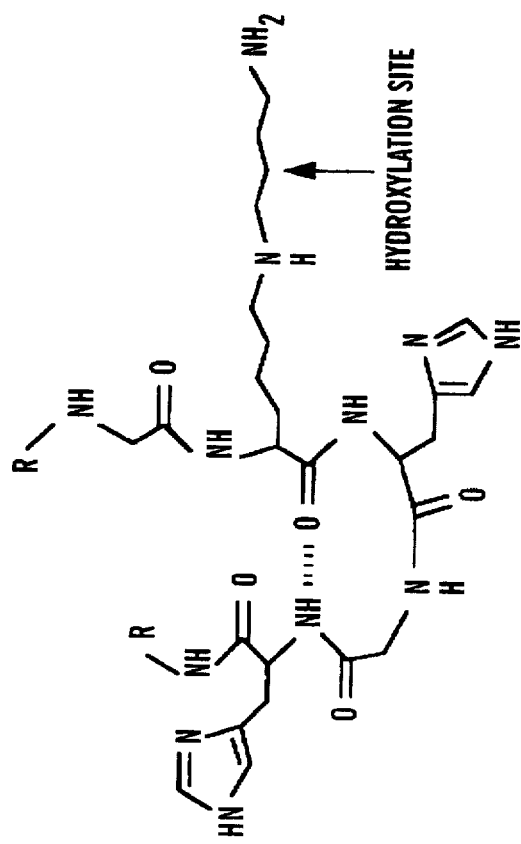
FIG. 2a shows the β-turn of a substrate motif.
Figure 2C:
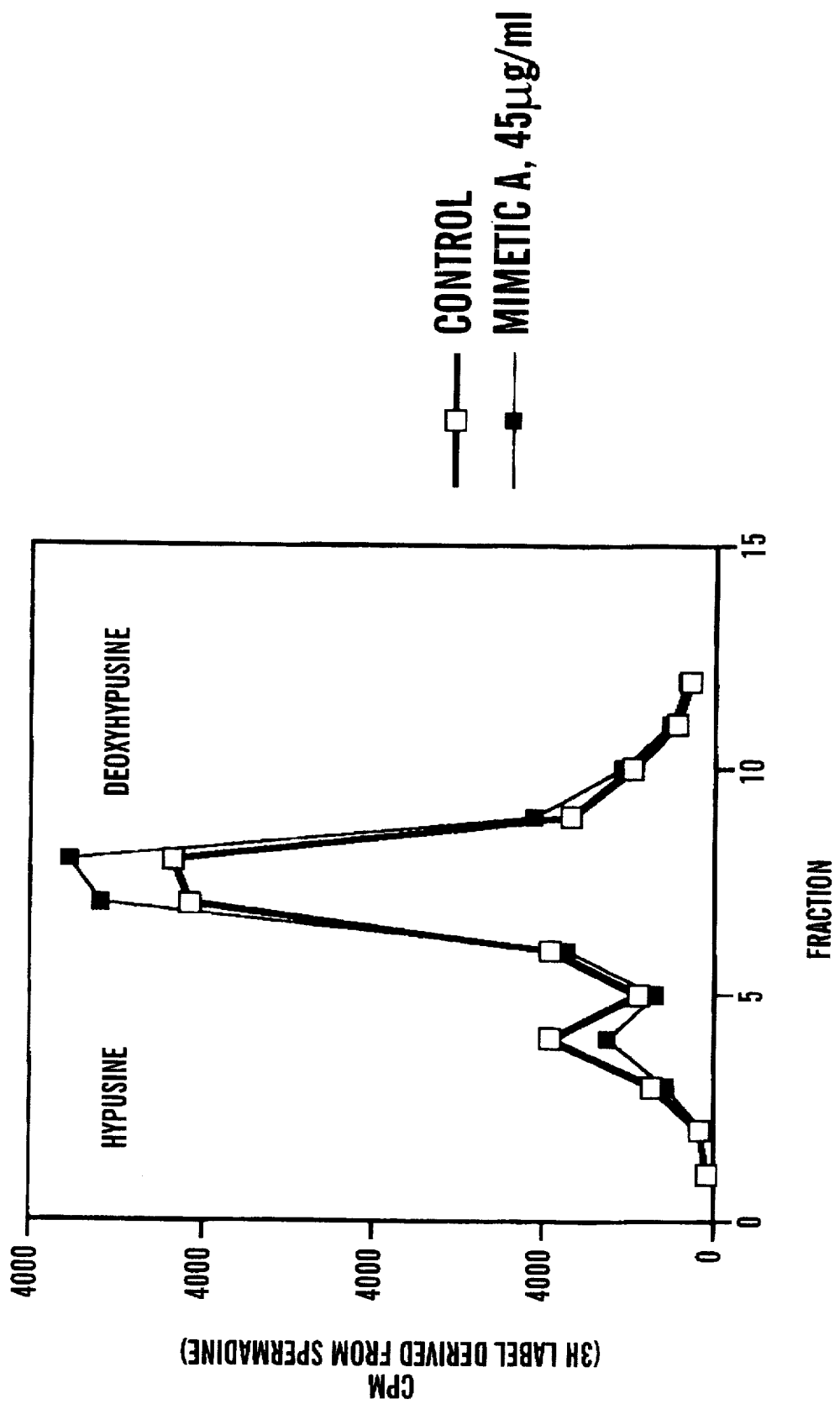
FIG. 2C shows the chromatographic profile of metabolically labeled hypusine/deoxyhypusine obtained after incubation of purified rat deoxyhypusyl hydroxylase with unhydroxylated eIF-5A in the absence (open squares) and presence of mimetic A (closed squares). Mimetic A is only weakly inhibitory itself, but useful as a carrier for appropriately positioned moieties of Formulae (I) or (II).

The effect of mimetic A on the hydroxylation of -G-x-y-G-containing proteins was studied using unhydroxylated eIF-5A precursor and purified deoxyhypusyl hydroxylase. As shown in FIG. 2a, the deoxyhypusine-to-hypusine conversion is suppressed by the presence of mimetic A, i.e., formation of the hydroxylated form is inhibited while the unhydroxylated precursor is not utilized. Mimetic A is only weakly inhibitory itself, but can be used to carry, positioned at the site of the asterisk in FIG. 2b, a "warhead" moiety of Formulae (I) or (II).

Example 3

Inhibition of Cellular Human Deoxyhypusyl Hydroxylase

The inhibiting effect of hydroxypyridones on the eIF-5A-hydroxylating enzyme was studied in cultured human cells (i.e. smooth muscle cells, B-lymphocytes).

Methods

DOHH Assay

The cellular conversion of the precursor deoxyhypusine to the hydroxylated hypusine in cells was examined, after preincubation with the inhibitor for 60 minutes, by labeling the human cells with $^3$H-spermidine (5 μCi/ml) in 25 cm$^2$ flasks (1×10$^6$ cells/flask) for 24 hours prior to cell lysis, precipitation with 10% TCA containing 1 mM each of putrescine, spermidine, and spermine, and hydrolysis in 6N HCl at 110° C. for 16 hours. The hydrolysate was analyzed for labeled amino acids on an amino acid analyzer by published methods (Park et al., *J. Biol. Chem.*, 257:7217–7222 (1982), which is hereby incorporated by reference). The retention of purified hypusine and deoxyhypusine was determined from standards.

Results

Figure 3A:
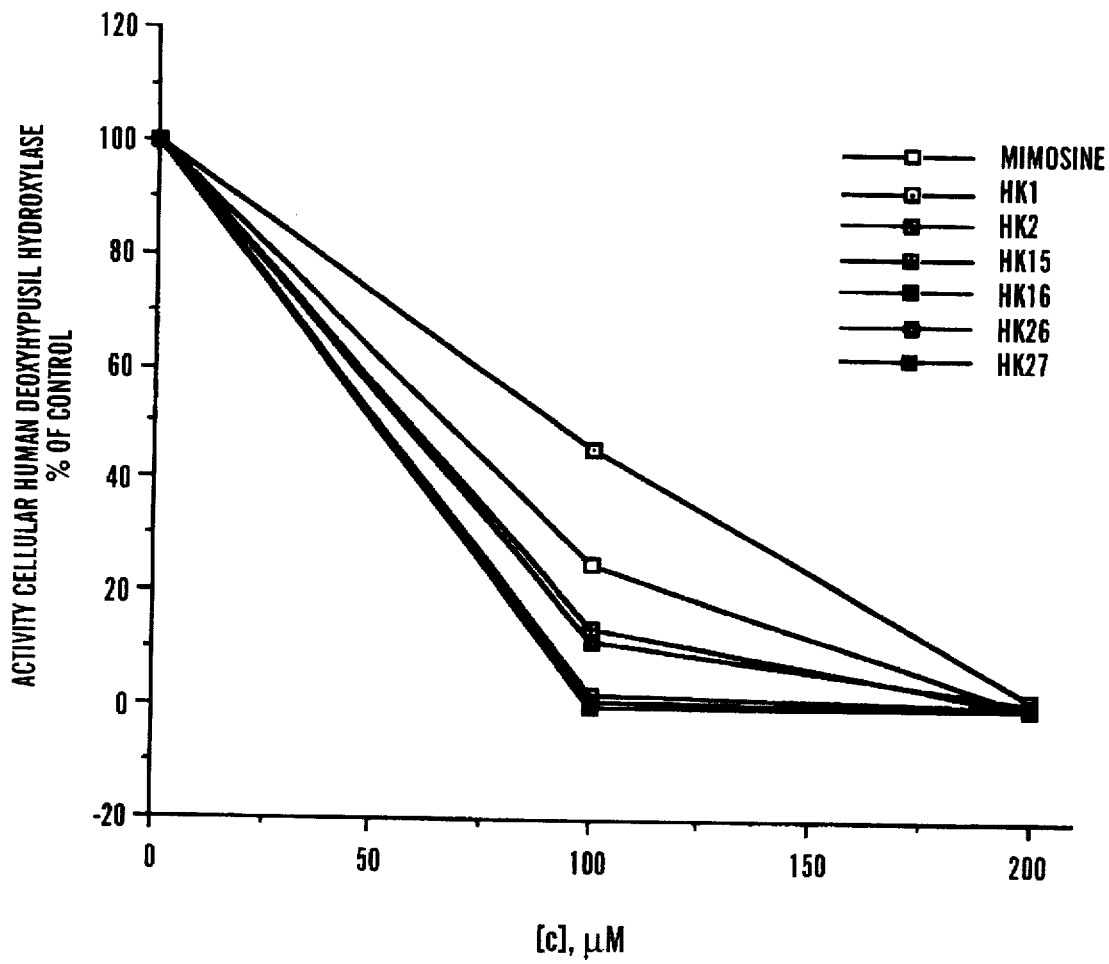
FIGS. 3a and 3b shows the inhibition of cellular human deoxyhypusyl hydroxylase, relative to uninhibited enzyme activity, by several representative hydroxypyridone compounds.
Figure 3B:
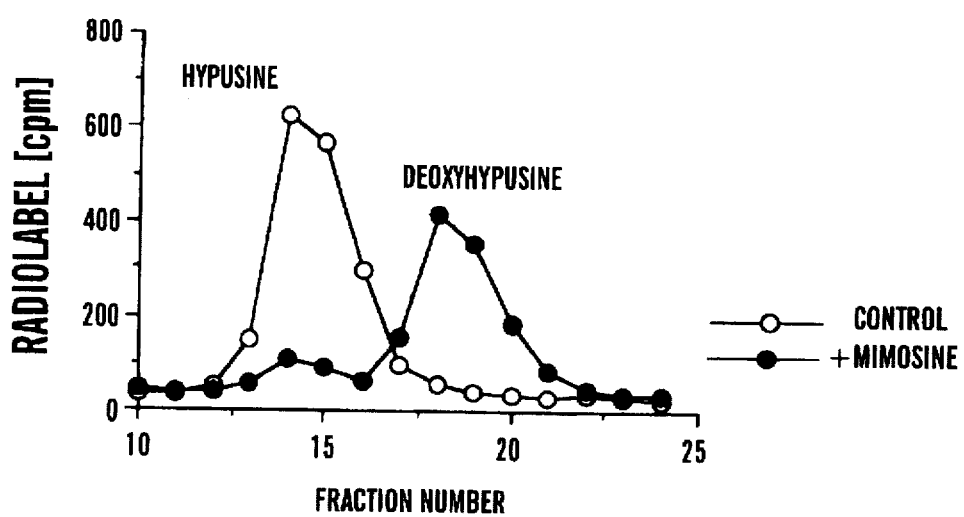

L-Mimosine is known to be a reversible inhibitor of the multiplication of certain cells, which is temporally associated with its ability to block the cellular deoxyhypusyl hydroxylase activity required to produce the active protein synthesis initiation factor eIF-5A (Hanauske-Abel et al., *Biochem. Biophys. Acta*, 1221:115–124 (1994), which is hereby incorporated by reference). The results presented in FIG. 3 indicate that L-mimosine and other representative hydroxypyridones also inhibit deoxyhypusyl hydroxylase activity in human smooth muscle cells (FIG. 3b) and in human B-lymphocytes (FIG. 3a).

Example 4

Inhibition of Prolyl 4-Hydroxylase in Scar Tissue-Producing Human Cells Obtained from Blood Vessels and Lung The selective inhibition of collagen secretion by illustrative hydroxypyridones was established in cultured human cells known to be causally linked to typical fibroproliferative diseases. The human cells used, vascular smooth muscle cells and lung fibroblasts, are generally believed to mediate all forms of vascular fibrosis and all forms of pulmonary fibrosis, respectively.

Methods

Cell Culture

A. Vascular Smooth Muscle Cells

Human coronary artery smooth muscle cells ("SMC") were isolated from specimens collected immediately after directional rotary atherectomy (Simpson AtheroCath, DVI, Inc., Redwood City, Calif.). A portion of the tissue was fixed in 10% buffered formalin for histology, and the remaining tissue was finely diced and placed onto collagen-coated (Vitrogen, Collagen Corp., Palo Alto, Calif.) flasks in Medium 199 containing 20% fetal bovine serum ("FBS") and gentamycin sulfate (50 ug/ml, Gibco, Grand Island, N.Y.). Cells migrating from the explants were subpassaged with trypsin/EDTA and used within the first 5 passages. Cell cultures were obtained from primary atherosclerotic and from restenotic lesions. To verify the SMC phenotype of the cultures, cells were plated onto LabTek 8-chamber slides and stained by indirect immunofluorescence for the SMC marker contractile α-actin, using a mouse monoclonal antibody specific for the contractile smooth muscle α-actin (clone No. 1A4; Sigma) which was detected with FITC- or peroxidase-labeled mouse immunoglobulins (Sigma). Non-immune mouse serum was used as a control. Results were photodocumented with a Nikon Labophot 2 fluorescence microscope.

B. Lung Fibroblasts

The established human lung fibroblast line MRC-5 was used, maintained, and propagated by routine cell culture techniques.

Assay of Cellular Human Prolyl 4-Hydroxylase

SMC or MRC-5 cells (3–5×10$^6$ cells/35 mm well) were labeled in the presence or absence of hydroxypyridones, with $^3$H-proline (Pro) (4 μCi/ml) for 24 hours in proline- and serum-free Dulbecco Minimal Essential Medium ("DMEM") containing 50 μg/ml sodium ascorbate and 20 μg/ml β-aminopropionitrile. Supernatants and cells were precipitated in 10% TCA, hydrolyzed (6N HCl, 110° C., 16 hours) and lyophilized, as described by G. Tschank, H. M. Hanauske-Abel and collaborators, *Biochem. J.* 248:625–633 (1987), which is hereby incorporated by reference. The hydrolysate was derivatized with phenylisothiocyanate and analyzed for $^3$H-proline ("Pro") and $^3$H-hydroxyproline ("Hyp") by HPLC on a reverse-phase C18 column, using an automated HPLC system (Hewlett-Packard, Wilmington, Del.) with an in-line scintillation counter (Inus Systems, Inc., Tampa, Fla.). The position of proline and hydroxyproline was determined from tritiated standards.

Plasminogen Activator Inhibitor Assay

Supernatants of human SMC incubated with the hydroxypyridone L-mimosine under serum-free conditions (to avoid plasma-derived inhibitors) were tested for their ability to inhibit a standard amount of urokinase-type plasminogen activator (uPA) in the presence of plasminogen and the fluorometric peptide plasmin substrate d-Val-Leu-Lys-aminomethylcoumarin (Enzyme Systems, Livermore, Calif.). Inhibition of plasmin generation was compared to a standard curve of human PAI-1 (American Diagnostica, Greenwich, Conn.) to yield PAI-1 activity.

Determination of Type I and Type III Procollagen Biosynthesis

SMC or MRC-5 cells (3–5×10$^6$ cells/35 mm well), incubated in serum-free DMEM containing 50 μg/ml sodium ascorbate and 20 μg/ml β-aminopropionitrile, are exposed for 24 hours to increasing concentrations of hydroxypyridones. After centrifugation, to clear any cellular debris, these supernatants are used to determine the levels of type I and III procollagens, using commercially available radioimmunoassays (Incstar and Behringwerke, respectively).

Determination of Type I and Type III Procollagen Biosynthesis

Human SMC (3–5×10$^5$ cells/35 mm well), grown to confluency and incubated in serum-free DMEM containing 50 μg/ml sodium ascorbate and 20 μg/ml β-aminopropionitrile, were exposed for 24 hours to increasing concentrations of test compounds. After centrifugation to clear any cellular debris, these supernatants were used to determine the levels of type I and III procollagens. Type I procollagen biosynthesis also was quantified by Western analysis in the following manner. Supernatants were precipitated with 10% TCA and electrophoresed under non-reducing conditions on a 4–20% SDS-PAGE gel. The gel was transferred to nitrocellulose with a semi-dry blotter (Bio-Rad, Hercules, Calif.). The membrane was blocked with 1% goat serum/1% bovine serum albumin and then incubated with a 1:200 dilution of a rabbit polyclonal antiserum (LF41) against a 21 amino acid synthetic peptide homologous to the C-terminal sequence of the C-propeptide of the component α1 chain of human type I procollagen. Because in each type I procollagen molecule two of these globular domains are disulfide-linked to the C-terminal globular domain of one component α2 chain, this antibody can be used under non-reducing conditions to detect trimeric, native C-propeptide proteolytically released during procollagen-collagen conversion. Non-immune rabbit serum was used as a control. Immunoblots were scanned with a UMAX UC630 flatbed scanner and quantified densitometrically using standard software.

Results

A high percentage (30–40%) of cultured SMC spontaneously showed strong reactivity toward the anti-α-actin antibody, and essentially all cells became α-actin positive upon serum-withdrawal and treatment with transforming growth factor-β1 (<1 ng/ml), consistent with the behavior of normal SMCs [Bjorkerud et al., *Arteriosclerosis*, 11:892–202 (1991)] or myofibroblasts [Desmouliere et al., *Cell Biol.*, 122:103–111 (1993); Ronnov-Jessen et al., *Lab. Invest.*, 68:696–707 (1993), which are hereby incorporated by reference]. The characteristic microscopic appearance of SMC after immunostaining for α-actin is shown in FIG. 4b and FIG. 4c. The cultured MRC-5 cells had the typical morphology of fibroblasts.

Figure 4A:
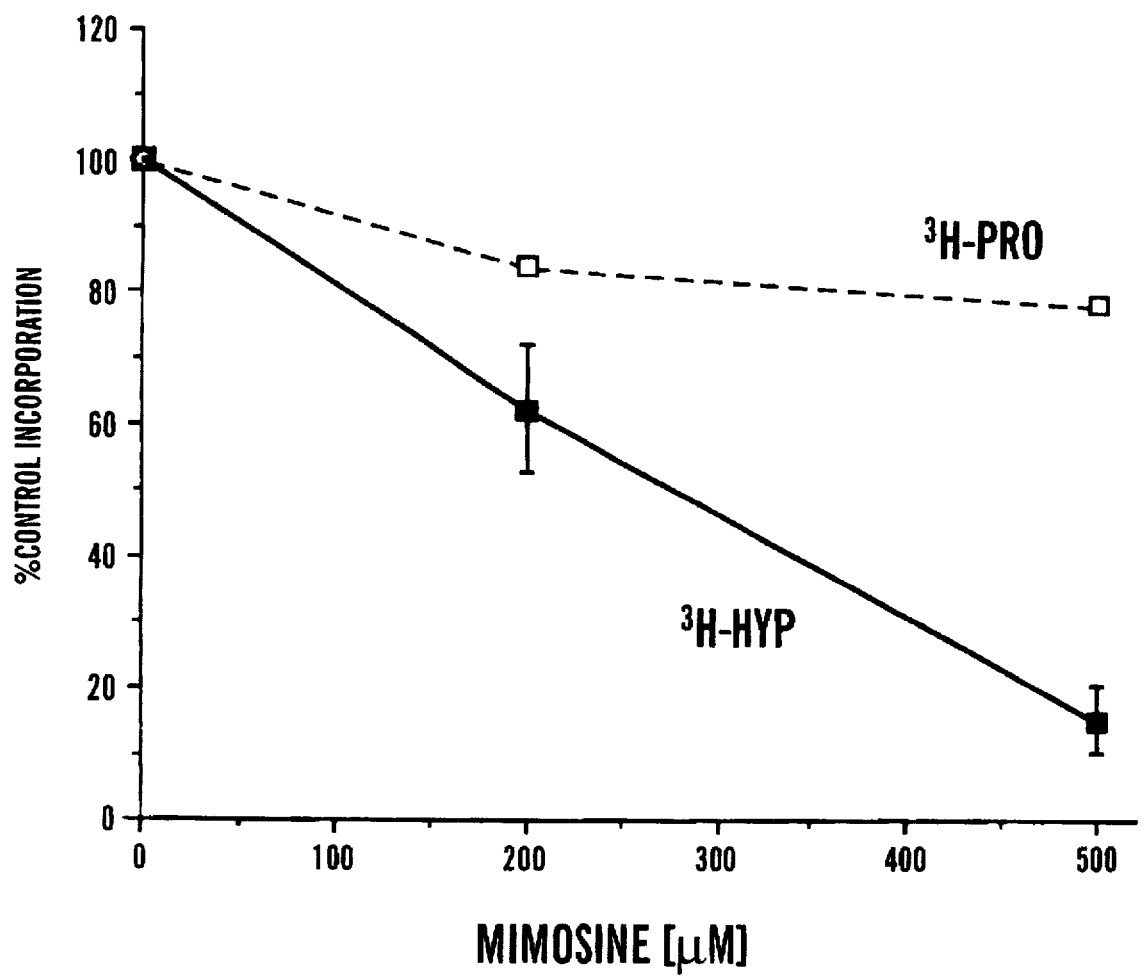
FIG. 4a shows, as percent of uninhibited controls, the suppressive effect of L-mimosine on prolyl 4-hydroxylation in cultured human smooth muscle cells ("SMC") obtained from coronary restenotic lesions. Those SMC, immunocytochemically identified by reactivity to contractile α-actin as shown in FIGS. 4b and 4c, were pretreated with inhibitor for 30 minutes prior to routine metabolic labeling with tritiated proline ("$^3$H-Pro") for 24 hours, followed by standard hydrolysis and separation of amino acids from both supernatant and cells. The degree of inhibition of scar collagen formation was determined by measuring formation of tritiated hydroxyproline ("$^3$H-Hyp").
Figure 4B:
Figure 4C:
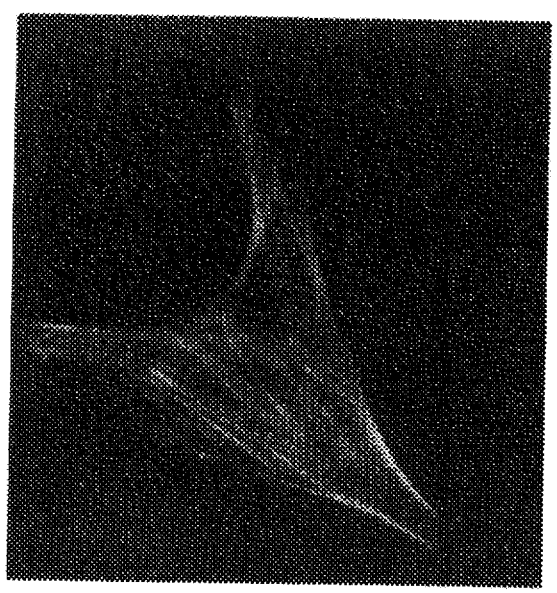
Figures 5A, 5B, 5C:
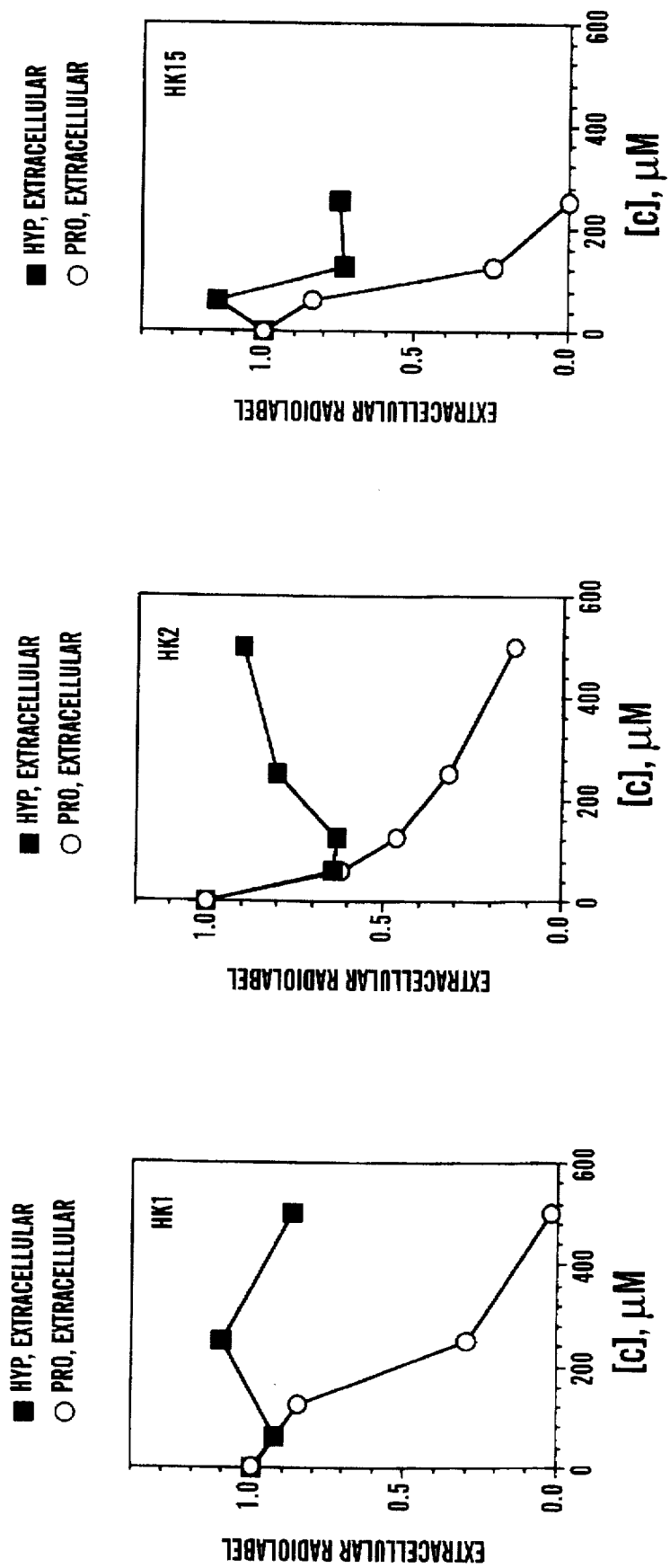
FIGS. 5a–f shows, as percent of uninhibited controls, the suppressive effect of six hydroxypyridone compounds on prolyl 4-hydroxylation in a human lung fibroblast line ("MRC-5"). Those cells were pretreated with inhibitor for 30 minutes prior to routine metabolic labeling with tritiated proline ("Pro") for 24 hours, followed by standard hydrolysis and separation of amino acids from both supernatant and cells for determination of proline conversion into hydroxyproline ("Hyp"). To demonstrate the selective inhibition of collagen secretion by these compounds, the extracellular counts representing Hyp within collagen proteins and the extracellular counts representing Pro within non-collagen proteins were determined by standard methods, then normalized to 1 million cells and expressed relative to uninhibited controls.
Figures 5D, 5E, 5F:
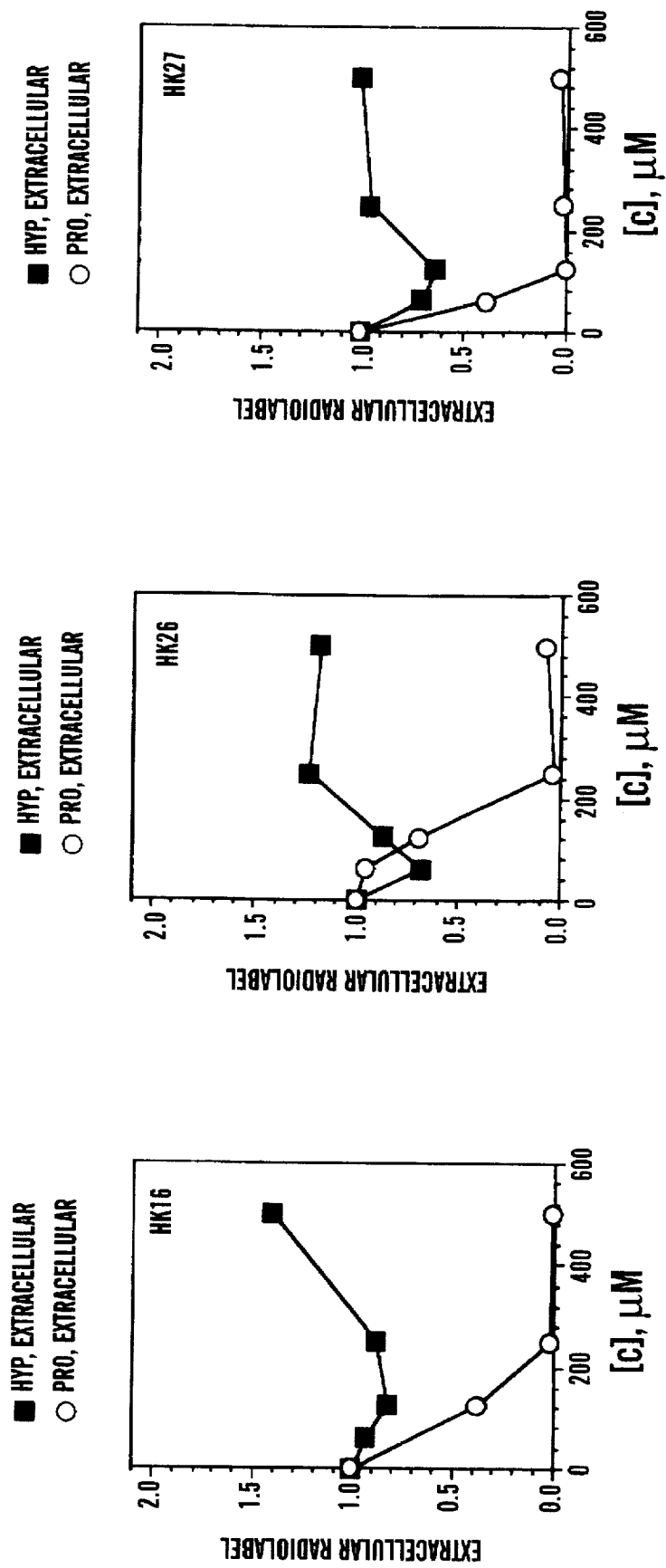

In these lesion-derived human SMC, the hydroxypyridone L-mimosine was able to selectively suppress hydroxyproline ("Hyp") formation by 80–90% whereas proline ("Pro") incorporation, an index of general protein synthesis, was reduced by less than 20% of controls (FIG. 4a). This indicates that L-mimosine quite selectively inhibits collagen hydroxylation, with minimal if any consequence for the overall synthesis of cellular proteins. Furthermore, the suppression of cellular prolyl hydroxylase activity by L-mimosine was rapidly reversible upon removal of the inhibitor. L-Mimosine also selectively inhibited the secretion of hydroxyproline-containing proteins by human lung fibroblasts. The discriminatingly suppressive effect by other illustrative hydroxypyridones on collagen secretion by these cells is evidenced in FIGS. 5a–f.

Selectivity for inhibition of just collagen secretion by SMC was also demonstrated when secreted proteins were determined individually. Three representative molecules excreted by vascular SMC were measured:

- the amino-terminal propeptide of type III procollagen, a marker of the fibrotic changes in atherosclerosis (Bonnet et al., *Eur. J. Clin. Invest.*, 18:18–21 (1988), which is hereby incorporated by reference);

- the carboxy-terminal propeptide of type I procollagen, a collagen expressed by SMC after vascular injury in vivo (Majesky et al., *J. Clin. Invest.*, 88:904–910 (1991), which is hereby incorporated by reference);
(NOTE: The procollagen propeptides are globular domains cleaved from the procollagen molecule after its secretion by the action of specific extracellular proteinases prior to collagen fibril formation, and thus are markers for extracellular collagen deposition.)

- plasminogen activator inhibitor-1 ("PAI-1"), a modulator of blood coagulation.

Figure 6A:
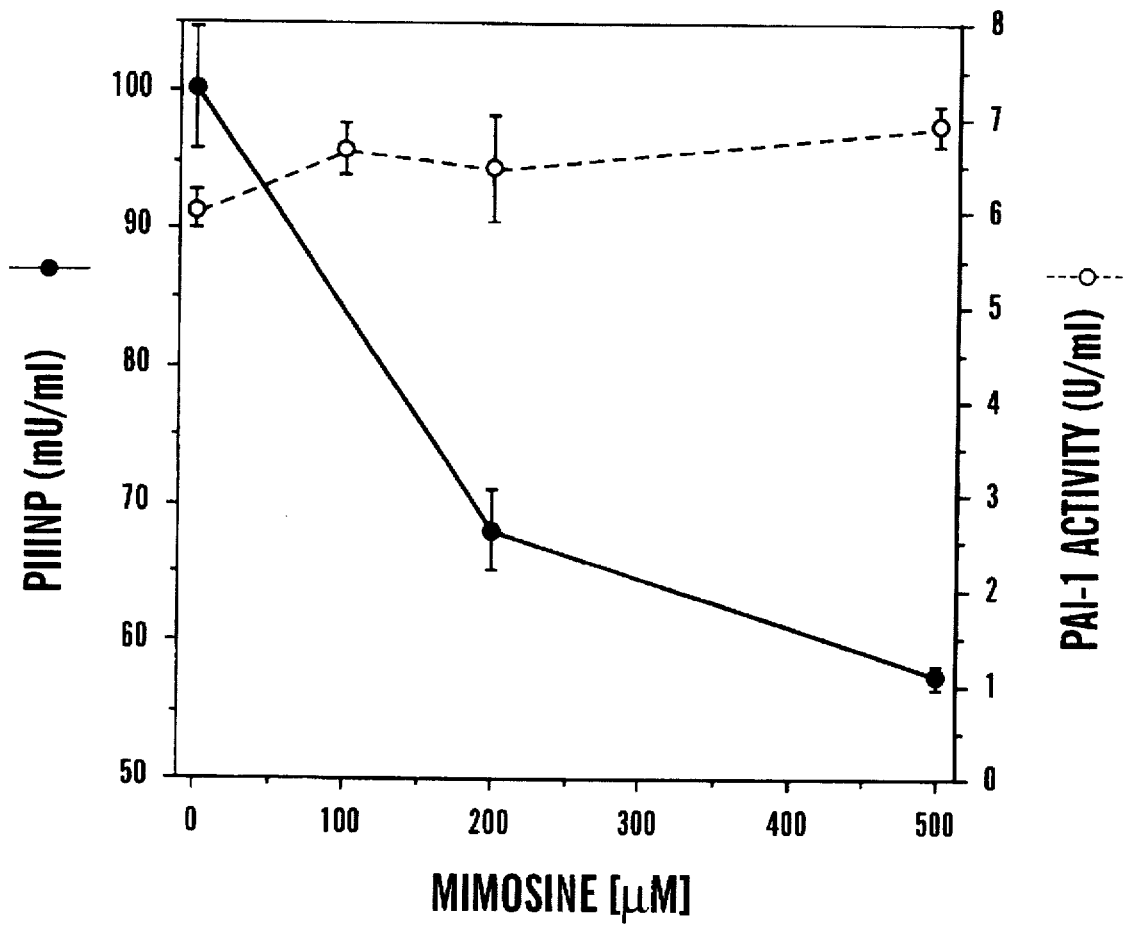
FIGS. 6a and 6b show the selectively suppressive effect of the representative hydroxypyridone L-mimosine on only the secretion of human type I and III collagens, but not on release of plasminogen activator inhibitor-1 ("PAI-1") activity, as produced by cultured human SMC obtained from restenotic coronary lesions. Type III collagen biosynthesis (FIG. 6a) was assessed by a commercial radioimmunoassay using a monoclonal antibody to the N-terminal propeptide of type III procollagen. Plasminogen activator inhibitor-1 ("PAI-1") activity was measured by a standard enzymatic method. Type I collagen biosynthesis (FIG. 6b) was assessed by routine Western blot using a monoclonal antibody to the C-terminal propeptide of type I procollagen.
Figure 6B:
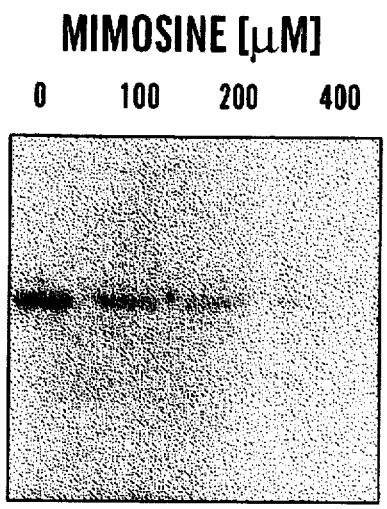

The results indicate that L-mimosine was a potent inhibitor of the secretion of procollagen types I and III. In contrast, the secretion of the non-collagenous protein, plasminogen activator inhibitor-1 ("PAI-1") was not affected by L-mimosine treatment (FIG. 6).

Example 5

Reversible Inhibition of Vascular Cell Proliferation

The selective inhibition of cell proliferation by illustrative hydroxypyridones was established in cultured human SMC obtained from fibroproliferative vascular lesions as described before.

Methods

Cell Proliferation

Inhibition of DNA synthesis was examined by semiautomated methods. SMC were plated at $1\times10^4$ cells/well in 96-well microtiter plates at least 24 hours prior to the assay. Agents were introduced into normal serum-containing growth media for 20 hours before the cells were pulsed with $^3$H-thymidine (1 µCi/ml) for 4 hours. Cells were collected with a cell harvester and the DNA-incorporated label determined by scintillation counting (Betaplate; Wallac, Inc., Gaithersburg, Md.) (n=6 per point).

Results

Figure 7:
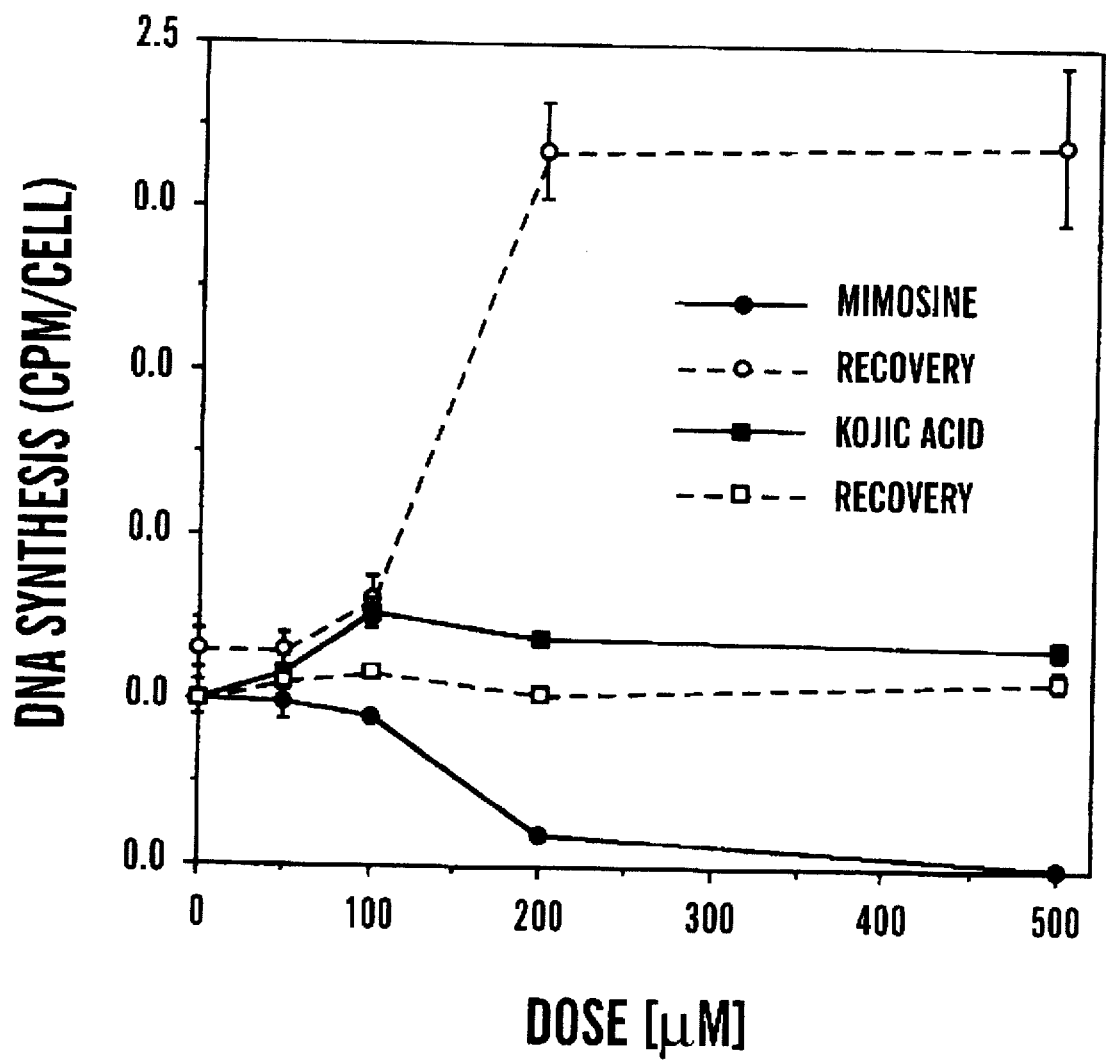
FIG. 7 shows the non-toxic reversibility of the inhibitory effect of hydroxypyridones on cell proliferation, as exemplified by the effect of L-mimosine on the proliferation of SMC derived from human coronary atherosclerotic lesions. The effect of the structural hydroxypyridone analog kojic acid is shown for comparison. Serum-stimulated DNA synthesis in SMC was determined by a 4-hour pulse of $^3$H-thymidine given 20 hours after treatment with L-mimosine and kojic acid (filled symbols). Identically treated, but unlabeled cells cultured in parallel, at that time point were washed and returned to fresh culture media without inhibitor for an additional 20 hours prior to otherwise identical labeling with $^3$H-thymidine (open symbols). Data is expressed as $^3$H-thymidine incorporated per cell to compensate for the reduced cell number in the wake of inhibitor treatment.

All hydroxypyridones were potent inhibitors of DNA synthesis in lesion-derived SMC. SMC obtained from both primary atherosclerotic and restenotic lesions were equally susceptible. To rule out toxicity-induced loss of viability, the reversibility of this effect was investigated. The cytostatic effect was fully reversible upon withdrawal of the compounds when corrected for cell number, as shown in FIG. 7 for the hydroxypyridone mimosine. After an initial 24-hour treatment, DNA synthesis was inhibited by L-mimosine, but not by the hydroxypyridone analog kojic acid. Following inhibitor removal and an additional 24-hour recovery period, there was a marked rebound effect on DNA synthesis in L-mimosine-arrested cells, but not in kojic acid-treated cells. This finding is consistent with synchronous release of a large cohort of SMC from a L-mimosine-sensitive arrest point, as observed in other cell types (Hanauske-Abel et al., *Biochem. Biophys. Acta* 1221:115–124 (1994), which is hereby incorporated by reference).

DISCUSSION

The body's response to any kind of real or perceived tissue damage consists of the activation of two major biochemical pathways, one resulting in the proliferation of cells, the other in the deposition of extracellular matrix at the site of the inciting event. The biological outcome of both coordinated pathways is the local formation of a fibrocellular tissue that usually serves to repair any lesion and to reconstruct physical integrity. This basic response is, however, often itself the cause for progressive loss of function, particularly, if this response causes disruption of the normal anatomy by scar tissue. Such a scarring (i.e., its fibroproliferative component) is a critical element of all human chronic diseases and is the key outcome-determining event in, for instance, liver cirrhosis, lung fibrosis, or restenosis of occluded blood vessels after interventional therapy.

To this day, cell proliferation and matrix formation are generally considered to be two interrelated, but disparate biological processes, with no common single chemical event controlling their execution. However, such a common single chemical event does exist. Cell proliferation and matrix formation each critically depend on the hydroxylation of specific proteins. Surprisingly, inhibitors of this common chemical event that block the scar-formation-mediating protein hydroxylases and thus have anti-fibroproliferative effects are identified. A general strategy for the further, rational design of such agents also has been formulated. This strategy centers on the combination of two molecular fragments, one imitating the substrate motif of the protein hydroxylases ("carrier"), the other one ("a warhead") consisting of a moiety able to interact with the active site metal of these enzymes. While each fragment by itself is not an efficient inhibitor, their combination into one agent by appropriate coupling, provides a superior agent for inhibition of protein hydroxylase activity ("warhead strategy").

Variations of carriers and warheads can be made by those skilled in the art guided by the warhead strategy, without departing from the spirit and scope of this strategy.

One class of warheads might be selected from agents that by themselves are able to interact with metal ions in solution (i.e. chelators). In this manner, the metal-dependent protein hydroxylases are depleted of their actual catalyst. However, the metal binding capacity of chelators does not determine, or correlate with, their ability to inhibit the protein hydroxylases. For instance, it was demonstrated for deoxyhypusyl hydroxylase that less efficient chelators achieved higher inhibitory effectiveness, indicating that a warhead must be able to reach physically the active site metal center, or otherwise is excluded from access by protein-imposed ionic and steric restrictions, as shown by Abbruzzese, Hanauske-Abel et al., *Biochim. Biophys. Acta* 1077:159–166 (1991), which is hereby incorporated by reference. Similarly, exposure of cells to metal chelators does not per se result in any antiproliferative effect. For instance, exposure to the chelator pyridoxal isonicotinyl hydrazone even stimulates the proliferation of certain human cells. See Ekblom et al., *Scand. J. Haematol.* 36:258–262 (1986), which is hereby incorporated by reference. Consequently, the highly selective inhibitory effect of metal-binding warheads, like the compounds of Formulae (I) and (II), on protein hydroxylation-related events and not, for instance, on protein synthesis in general, is surprising.

It has been noted before that the protein hydroxylases share common features, such as the use of similar substrate motifs by prolyl 4-hydroxylase and deoxyhypusyl hydroxylase. However, this does not mean that inhibitors identified for one of these enzymes will also inhibit the other enzymes, such as inhibitors structurally suited to bind the active site metal of these enzymes. For example, pyridine-2,4-dicarboxylate, which binds to the active site metal ion of prolyl 4-hydroxylase and, consequently, is an excellent inhibitor of collagen formation, as described by Majamaa, Hanauske-Abel et al., *Eur. J. Biochem.* 138:239–245 (1984), which is hereby incorporated by reference, is non-inhibitory for deoxyhypusyl hydroxylase, as determined by Abbruzzese et al., *J. Biol. Chem.* 261:3085–9 (1986), which is hereby incorporated by reference. Likewise, certain catecholpeptides have been identified as competitive, potent inhibitors of purified deoxyhypusyl hydroxylase but were found to be only weak or non-competitive inhibitors for prolyl 4-hydroxylase (Abbruzzese, Hanauske-Abel, et al., *Biochim. Biophys. Acta*, 1077:159–166 (1991), which is hereby incorporated by reference), reemphasizing the distinct active site organization of each protein hydroxylase. Consequently, the discovery that a single class of agents simultaneously and potently inhibits both prolyl 4- and deoxyhypusyl hydroxylase, whether purified or in cells, is surprising and points to a unique effect of these agents on the formation of the hydroxylated amino acid residues.

In collagens, the crucial hydroxylated residues are trans-4-hydroxyprolines, formed post-translationally by prolyl 4-hydroxylase. This enzyme, an $\alpha_2\beta_2$-tetrameric, divalent iron-containing dioxygenase, stoichiometrically utilizes 2-oxoglutarate and molecular oxygen for the stereospecific hydroxylation of a sequence-defined proline residue, generating equimolar quantities of carbon dioxide, succinate, and peptidyl trans-4-hydroxyproline. One atom of molecular oxygen appears in the hydroxyl group, the other one in the 2-oxoglutarate-derived succinate (Kivirikko et al., *FASEB J.*, 3:1609–1617 (1989), which is hereby incorporated by reference). Ascorbate is not consumed stoichiometrically, and the catalytic cycle proceeds even in its absence (Myllyla et al., *J. Biol. Chem.*, 259:5403–5405 (1984), which is hereby incorporated by reference). The stereochemical concept for the mechanism of prolyl 4-hydroxylase, published in 1982 by Hanauske-Abel and Gunzler (*J. Theor. Biol.* 94:421–455 (1982), which is hereby incorporated by reference), was the first to accommodate these complex findings and since then has been used successfully to guide the development of inhibitory 2-oxoglutarate analogs. Suppression of prolyl 4-hydroxylation prevents the formation of the collagenous triple helix which is entirely dependent on trans-4-hydroxyproline residues and is required for the secretion and processing of at least the interstitial procollagens. In this way, inhibition of prolyl 4-hydroxylase markedly and selectively reduces formation of the extracellular matrix (Hanauske-Abel, *J. Hepatol.*, 13 (suppl.):s8–s15) (1991), which is hereby incorporated by reference).

In eIF-5A, this unique hydroxylated amino acid residue is hypusine [$N^\epsilon$-(4-amino-2(R)-hydroxybutyl)lysine]. The synthesis of active eIF-5A involves two distinct post-translational modifications: i) the $NAD^+$-dependent transfer of a spermidine-derived 4-aminobutyl moiety onto the $\epsilon$-amino group of a sequence-defined lysine residue, generating deoxyhypusine (Wolf et al., *J. Biol. Chem.*, 265:4793–4799 (1990), which is hereby incorporated by reference); and ii) the stereospecific hydroxylation of carbon 9 by the metallo-enzyme deoxyhypusyl hydroxylase, generating hypusine (Abbruzzese et al., *J. Biol. Chem.*, 261:3085–3089 (1986), which is hereby incorporated by reference). eIF-5A contains a single hypusine residue that has not been identified in any other protein (Park et al., *Bio Factors*, 4:95–104 (1993), which is hereby incorporated by reference). Inhibition of hypusine formation correlates with reversible arrest of cell proliferation, apparently by selectively inhibiting polysomal production of certain proteins indispensible for the onset of DNA replication, thereby causing the reversible accumulation of cells in the late G1 phase of the cell cycle (Hanauske-Abel et al., *Biochim. Biophys. Acta* 1221: 115–24, (1994), which is hereby incorporated by reference).

As the collagens do not contain hypusine and as eIF-5A lacks hydroxyproline, it would not have been expected that inhibition of just one of the protein hydroxylases could by itself produce an anti-fibroproliferative effect. In fact, experimental evidence suggests that cross-over inhibition of proliferation does not occur if collagen hydroxylation is directly and selectively suppressed: the potent prolyl 4-hydroxylase antagonists pyridine 2,4-dicarboxylate and pyridine 2,5-dicarboxylate (Majamaa et al., *Eur. J. Biochem.*, 138:239–245 (1984), which is hereby incorporated by reference), which lack the ability to inhibit deoxyhypusyl hydroxylase (Abbruzzese et al., *J. Biol. Chem.*, 261:3085–3089 (1986), which is hereby incorporated by reference), do not affect cell proliferation or cell cycle transit.

The single most important cellular protein hydroxylases determining collagen secretion and cell proliferation, prolyl 4-hydroxylase and deoxyhypusyl hydroxylase, respectively, are each inhibited by compounds of Formulae (I) or (II) in a dose-dependent manner (Table II). The hydroxypyridones L-mimosine and HK1, DMPH, for instance, directly inhibit prolyl 4-hydroxylase (FIG. 1) and deoxyhypusyl hydroxylase (FIG. 3) when assayed in vitro. The inhibition of each cellular protein hydroxylase has been shown before to halt the secretion of de novo synthesized collagens (Hanauske-Abel, *J. Hepatol.*, 13 (suppl. 3):s8–s15) (1991), which is hereby incorporated by reference) and to arrest the onset of DNA synthesis, respectively (Hanauske-Abel et al., *Bio-* chim. Biophys. Acta 1221: 115–24 (1994), which is hereby incorporated by reference), a finding corroborated by the incorporation of radiolabeled precursors (FIGS. 4, 5, 7). Each of these suppressive effects was reversible upon removal of L-mimosine and HK1, respectively, and did not result from non-specific or toxic effects (FIGS. 6, 7).

Although the invention has been described in detail for the purposes of illustration, it is understood that such detail is solely for that purpose, and variations can be made by those skilled in the art without departing from the spirit and scope of the invention that is defined by the following claims.

What is claimed:

1. A method of suppressing formation of collagen or biosynthesis of procollagen in living systems comprising:

administering to living systems an amount of a compound of formulas I or II and their salts, esters, or amides effective to suppress the formation of collagen or biosynthesis of procollagen as follows:

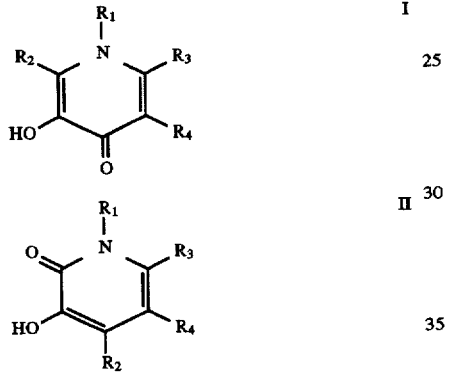

$R_1$, $R_2$, $R_3$, and $R_4$ each individually represent a hydrogen, an alkyl, alkenyl, or alkoxy group containing 1 to about 8 carbon atoms, an aryl, aralkyl, or cycloalkyl group containing about 5 to 12 carbon atoms, or a carboalkoxy or carbamyl group containing up to 8 carbon atoms, or a peptide or peptidomimetic moiety containing 10 to about 30 carbon atoms, with the proviso that where $R_1$ is hydrogen, any group $R_2$ or $R_3$ containing carbamyl functionality up to 8 carbon atoms consists of only carbamyl functionality of up to 8 carbon atoms, wherein the compound is not mimosine.

2. A method according to claim 1, wherein $R_2$ is H or an alkyl group with up to 2 carbon atoms and $R_3$ and $R_4$ is H or methyl.

3. A method according to claim 2, wherein $R_1$ and $R_2$ are methyl and $R_3$ and $R_4$ are H.

4. A method according to claim 2, wherein $R_1$ is $CH_2CH_2OCH_3$, $R_2$ is methyl, and $R_3$ and $R_4$ are H.

5. A method according to claim 2, wherein $R_1$ is $CH_2CH=CH_2$, $R_2$ is methyl, and $R_3$ and $R_4$ are H.

6. A method according to claim 2, wherein $R_1$ is ethyl, $R_2$ is methyl, and $R_3$ and $R_4$ are H.

7. A method according to claim 2, wherein $R_1$ is $(CH_2)_2CH_3$, $R_2$ is methyl, and $R_3$ and $R_4$ are H.

8. A method according to claim 1, wherein $R_1$, $R_2$, $R_3$, and/or $R_4$ is a peptide or peptidomimetic moiety.

9. A method of treating a patient with a fibrotic or fibroproliferative disorder characterized by excessive formation of scar tissue comprising:

administering to a patient an effective amount of a compound of formulas I or II and their salts, esters, or amides as follows:

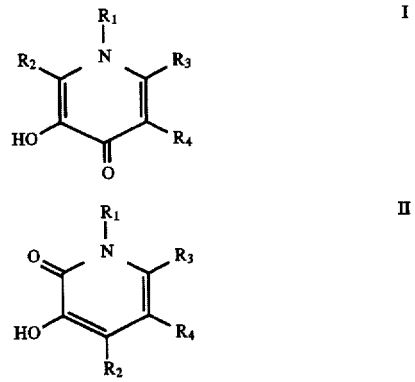

$R_1$, $R_2$, $R_3$, and $R_4$ each individually represent a hydrogen, an alkyl, alkenyl, or alkoxy group containing 1 to about 8 carbon atoms, an aryl, aralkyl, or cycloalkyl group containing about 5 to 12 carbon atoms, or a carboalkoxy or carbamyl group containing up to 8 carbon atoms, or a peptide or peptidomimetic moiety containing 10 to about 30 carbon atoms, with the proviso that where $R_1$ is hydrogen, any group $R_2$ or $R_3$ containing carbamyl functionality of up to 8 carbon atoms consists of only carbamyl functionality of up to 8 carbon atoms.

10. A method according to claim 9, wherein said fibrotic or fibroproliferative disorder is endogenously occurring, is caused by genetic abnormalities, is due to environmental agents, or is a tissue response to medical intervention.

11. A method according to claim 9, wherein said fibrotic or fibroproliferative disorder is hepatic fibrosis, liver cirrhosis, pulmonary fibrosis, restenosis, renal fibrosis, myclofibrosis, scleroderma, neonatal liver fibrosis, post-burn scarring, eye surgery scarring, or keloids.

12. A method according to claim 9, wherein said administering is carried out orally, intravenously, intramuscularly, intraperitoneally, subcutaneously, by intranasal instillation, by application to mucous membranes, and by instillation into hollow organ walls.

13. A method according to claim 9, wherein the compound is administered with a physiologically suitable vehicle.

14. A method according to claim 9, wherein $R_2$ is H or an alkyl group with up to 2 carbon atoms and $R_3$ and $R_4$ is H or methyl.

15. A method according to claim 14, wherein $R_1$ is $CH_2CH(COOH)NH_2$ and $R_2$, $R_3$, and $R_4$ are H.

16. A method according to claim 15, wherein the compound is L-mimosine.

17. A method according to claim 14, wherein $R_1$ and $R_2$ are methyl and $R_3$ and $R_4$ are H.

18. A method according to claim 14, wherein $R_1$ is $CH_2CH_2OCH_3$, $R_2$ is methyl, and $R_3$ and $R_4$ are H.

19. A method according to claim 14, wherein $R_1$ is $CH_2CH=CH_2$, $R_2$ is methyl, and $R_3$ and $R_4$ are H.

20. A method according to claim 14, wherein $R_1$ is ethyl, $R_2$ is methyl, and $R_3$ and $R_4$ are H.

21. A method according to claim 14, wherein $R_1$ is $(CH_2)_2CH_3$, $R_2$ is methyl, and $R_3$ and $R_4$ are H.

22. A method accoring to claim 9, wherein $R_1$, $R_2$, $R_3$, and/or $R_4$ is a peptide or peptidomimetic moiety.

23. A method of suppressing formation of collagen or biosynthesis of procollagen in living systems comprising:

administering to living systems an amount of a compound of formulas I or II and their salts, esters, or amides effective to suppress the formation of collagen or biosynthesis of procollagen as follows:

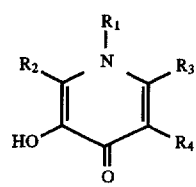

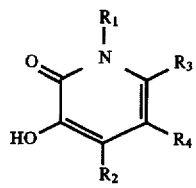

$R_1$, $R_2$, $R_3$, and 4 each individually represent a hydrogen, an alkyl, alkenyl, or alkoxy group containing 1 to about 8 carbon atoms, an aryl, aralkyl, or cycloalkyl group containing about 5 to 12 carbon atoms, or a carboalkoxy group containing up to 8 carbon atoms, or a peptide or peptidomimetic moiety containing 10 to about 30 carbon atoms, wherein the compound is not mimosine.

24. A method of treating a patient with a fibrotic or fibroproliferative disorder characterized by excessive formation of scar tissue comprising:

administering to a patient an effective amount of a compound of formulas I or II and their salts, esters, or amides as follows:

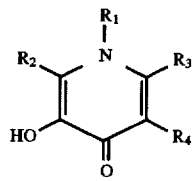

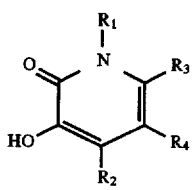

$R_1$, $R_2$, $R_3$, and $R_4$ each individually represent a hydrogen, an alkyl, alkenyl, or alkoxy group containing 1 to about 8 carbon atoms, an aryl, aralkyl, or cycloalkyl group containing about 5 to 12 carbon atoms, or a carboalkoxy group containing up to 8 carbon atoms, or a peptide or peptidomimetic moiety containing 10 to about 30 carbon atoms.

* * * * *